US012012591B2

(12) United States Patent
Liberti et al.

(10) Patent No.: US 12,012,591 B2
(45) Date of Patent: Jun. 18, 2024

(54) APPARATUS AND METHOD FOR IMMUNOMAGNETIC CELL SEPARATION

(71) Applicants: Joseph Francis Liberti, Harrison, NY (US); BIOMAGNETIC SOLUTIONS LLC., State College, PA (US)

(72) Inventors: Paul A. Liberti, Naples, FL (US); Todor R. Khristov, State College, PA (US); Dustin W. Ritter, State College, PA (US)

(73) Assignee: Biomagnetic Solutions LLC, State College, PA (US)

( * ) Notice: Subject to any disclaimer, the term of this patent is extended or adjusted under 35 U.S.C. 154(b) by 203 days.

(21) Appl. No.: 17/316,054

(22) Filed: May 10, 2021

(65) Prior Publication Data

US 2021/0261942 A1 Aug. 26, 2021

Related U.S. Application Data

(63) Continuation of application No. 15/569,587, filed as application No. PCT/US2016/031528 on May 9, 2016, now abandoned.

(60) Provisional application No. 62/158,845, filed on May 8, 2015, provisional application No. 62/213,575, filed on Sep. 2, 2015, provisional application No. 62/174,687, filed on Jun. 12, 2015.

(51) Int. Cl.
| *C12N 13/00* | (2006.01) |
|---|---|
| *A61M 1/36* | (2006.01) |
| *B01D 15/38* | (2006.01) |
| *B01F 31/23* | (2022.01) |
| *B01F 33/452* | (2022.01) |
| *B03C 1/01* | (2006.01) |
| *B03C 1/033* | (2006.01) |
| *B03C 1/034* | (2006.01) |
| *B03C 1/28* | (2006.01) |
| *G01N 33/543* | (2006.01) |

(52) U.S. Cl.
CPC ........... *C12N 13/00* (2013.01); *A61M 1/3618* (2014.02); *B01D 15/3885* (2013.01); *B01F 31/23* (2022.01); *B01F 33/452* (2022.01); *B03C 1/01* (2013.01); *B03C 1/0332* (2013.01); *B03C 1/034* (2013.01); *B03C 1/288* (2013.01); *G01N 33/54326* (2013.01); *B03C 2201/18* (2013.01); *B03C 2201/22* (2013.01); *B03C 2201/26* (2013.01)

(58) Field of Classification Search
None
See application file for complete search history.

(56) References Cited

U.S. PATENT DOCUMENTS

| 3,838,794 A | 10/1974 | Cogley et al. |
|---|---|---|
| 3,970,518 A | 7/1976 | Giaever |
| 4,018,886 A | 4/1977 | Giaever |
| 4,230,685 A | 10/1980 | Senyei et al. |
| 4,267,234 A | 5/1981 | Rembaum |
| 4,375,407 A | 3/1983 | Kronick |
| 4,452,773 A | 6/1984 | Molday |
| 4,554,088 A | 11/1985 | Whitehead et al. |
| 4,654,267 A | 3/1987 | Ugelstad et al. |
| 4,659,678 A | 4/1987 | Forrest et al. |
| 4,710,472 A | 12/1987 | Saur et al. |
| 4,795,698 A | 1/1989 | Owen et al. |
| 4,866,282 A | 9/1989 | Miripol et al. |
| 4,904,391 A | 2/1990 | Freeman |
| 4,910,148 A | 3/1990 | Sorenson et al. |
| 4,935,147 A | 6/1990 | Ullman et al. |
| 4,988,618 A | 1/1991 | Li et al. |
| 5,163,909 A | 11/1992 | Stewart |
| 5,186,827 A | 2/1993 | Liberti et al. |
| 5,194,145 A | 3/1993 | Schoendorfer |
| 5,297,234 A | 3/1994 | Harms et al. |
| 5,399,166 A | 3/1995 | Laing |
| 5,466,574 A | 11/1995 | Liberti et al. |
| 5,510,621 A | 4/1996 | Goldman |
| 5,512,332 A | 4/1996 | Liberti et al. |
| 5,514,340 A | 5/1996 | Lansdorp et al. |
| 5,536,475 A | 7/1996 | Moubayed et al. |
| 5,541,072 A | 7/1996 | Wang et al. |
| 5,567,326 A | 10/1996 | Ekenberg et al. |
| 5,597,531 A | 1/1997 | Liberti et al. |
| 5,660,990 A | 8/1997 | Rao et al. |
| 5,693,539 A | 12/1997 | Miltenyi et al. |
| 5,698,271 A | 12/1997 | Liberti et al. |
| 5,799,830 A | 9/1998 | Carroll et al. |
| 5,968,820 A | 10/1999 | Zborowski et al. |
| 6,036,857 A | 3/2000 | Chen et al. |
| 6,120,856 A | 9/2000 | Liberti et al. |
| 6,126,835 A | 10/2000 | Barbera-Guillem et al. |
| 6,129,848 A | 10/2000 | Chen et al. |
| 6,132,607 A | 10/2000 | Chen et al. |
| 6,190,913 B1 | 2/2001 | Singh |
| 6,245,570 B1 | 6/2001 | Grimm et al. |
| 6,251,295 B1 | 6/2001 | Johnson |
| 6,346,196 B1 | 2/2002 | Bose |
| 6,432,630 B1 | 8/2002 | Blankenstein |
| 6,551,843 B1 | 4/2003 | Rao et al. |

(Continued)

FOREIGN PATENT DOCUMENTS

| CA | 2067158 | * 3/1991 | ............. A61K 47/48 |
|---|---|---|---|
| CA | 2363548 A1 | 9/1996 | |

(Continued)

*Primary Examiner* — Ann Montgomery
(74) *Attorney, Agent, or Firm* — Howson & Howson LLP

(57) ABSTRACT

An apparatus and methods are provided for the magnetic separation of target bioentities. The apparatus includes a fluid chamber and a magnetic element for drawing target bioentities toward a collection surface of the fluid chamber. The apparatus may include a positioning assembly operable to variable change the position and orientation f the fluid chamber relative to the magnetic element.

20 Claims, 15 Drawing Sheets

(56) References Cited

U.S. PATENT DOCUMENTS

| | | |
|---|---|---|
| 6,576,458 B1 | 6/2003 | Sarem et al. |
| 6,623,982 B1 | 9/2003 | Liberti et al. |
| 6,764,859 B1 | 7/2004 | Kreuwel et al. |
| 7,241,281 B2 | 7/2007 | Coelho et al. |
| 7,476,543 B2 * | 1/2009 | Becker ................. G01N 1/2813 422/561 |
| 7,699,979 B2 | 4/2010 | Li et al. |
| 7,776,580 B2 | 8/2010 | Zhang et al. |
| 8,058,010 B2 * | 11/2011 | Erickson .......... G01N 35/00009 435/7.1 |
| 9,381,291 B2 | 7/2016 | Boggs et al. |
| 10,213,544 B2 | 2/2019 | Radwanski |
| 10,926,020 B2 | 2/2021 | Peritt et al. |
| 11,324,884 B2 | 5/2022 | Carbone et al. |
| 2002/0058030 A1 | 5/2002 | Monroy et al. |
| 2003/0060747 A1 | 3/2003 | Fries et al. |
| 2003/0127396 A1 | 7/2003 | Siddiqi |
| 2004/0124157 A1 | 7/2004 | Briggs et al. |
| 2004/0186412 A1 | 9/2004 | Mallett et al. |
| 2005/0121604 A1 | 6/2005 | Mueth et al. |
| 2005/0186669 A1 | 8/2005 | Ho et al. |
| 2007/0042490 A1 | 2/2007 | Welter et al. |
| 2007/0125942 A1 | 6/2007 | Kido |
| 2007/0160979 A1 * | 7/2007 | Andersson .............. B01L 3/508 435/5 |
| 2008/0152546 A1 * | 6/2008 | Bedingham ....... B01F 35/71725 137/485 |
| 2009/0053799 A1 | 2/2009 | Chang-Yen et al. |
| 2009/0188211 A1 | 7/2009 | Galliher et al. |
| 2009/0220932 A1 | 9/2009 | Ingber et al. |
| 2010/0081122 A1 | 4/2010 | Shibuya et al. |
| 2010/0112700 A1 | 5/2010 | Shaaltiel et al. |
| 2010/0129837 A1 | 5/2010 | Mach et al. |
| 2011/0020459 A1 | 1/2011 | Achrol et al. |
| 2011/0124128 A1 | 5/2011 | Oosterbroek et al. |
| 2011/0165666 A1 | 7/2011 | Dahle |
| 2012/0115167 A1 | 5/2012 | Chandler et al. |
| 2013/0075318 A1 | 3/2013 | Zhang et al. |
| 2013/0203049 A1 | 8/2013 | Corbett et al. |
| 2014/0120544 A1 * | 5/2014 | Brahmasandra .. B01L 3/502715 536/25.4 |
| 2014/0370592 A1 | 12/2014 | Miltenyi et al. |
| 2015/0064703 A1 * | 3/2015 | Super ............... G01N 33/56938 435/6.12 |
| 2015/0153259 A1 | 6/2015 | Liberti et al. |
| 2016/0015599 A1 | 1/2016 | Gentile et al. |
| 2017/0029776 A1 | 2/2017 | Cork et al. |
| 2017/0315121 A1 | 11/2017 | Wegener et al. |
| 2017/0335272 A1 | 11/2017 | Tsai et al. |
| 2018/0172685 A1 | 6/2018 | Wegener et al. |
| 2018/0291364 A1 | 10/2018 | Liberti et al. |
| 2019/0010435 A1 | 1/2019 | Norderhaugh et al. |
| 2019/0169594 A1 | 6/2019 | Zhang et al. |

FOREIGN PATENT DOCUMENTS

| | | |
|---|---|---|
| JP | 2010-096677 A | 4/2010 |
| WO | 90/04019 A1 | 4/1990 |
| WO | 91/11716 A2 | 8/1991 |
| WO | 2013/048546 A1 | 4/2013 |

* cited by examiner

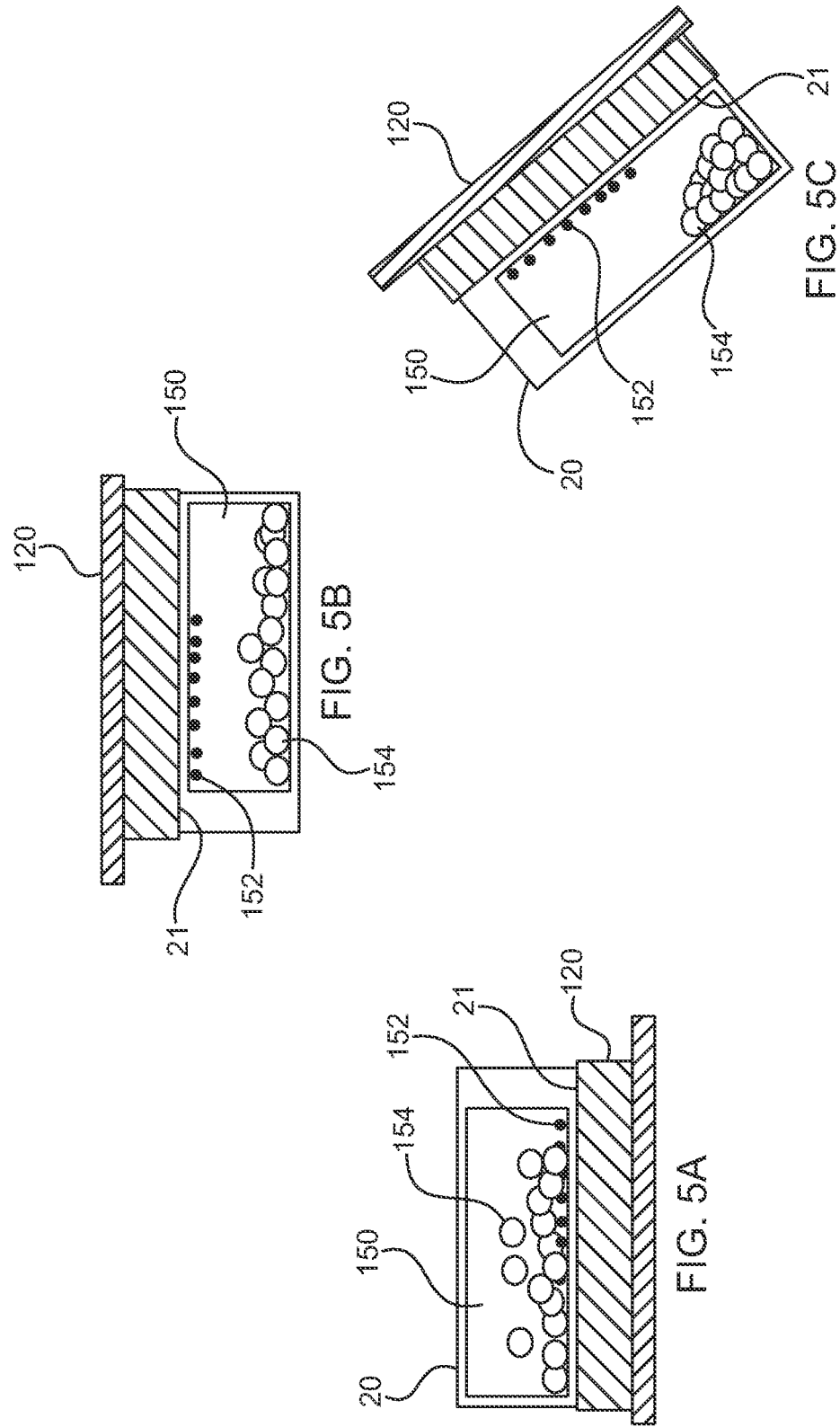

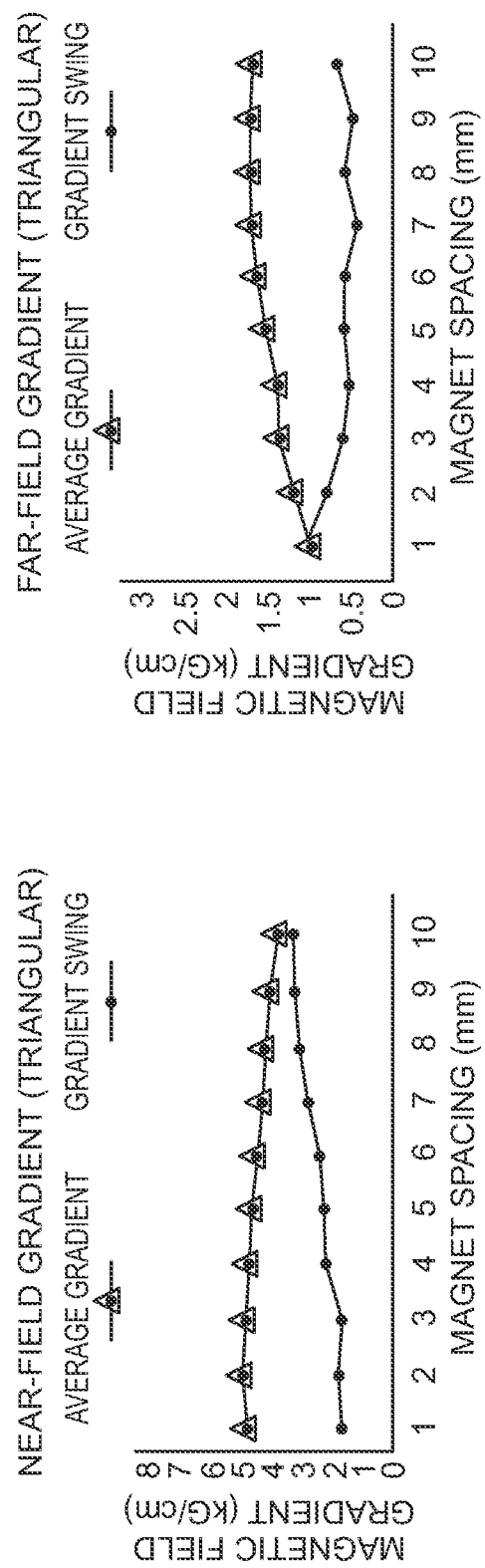
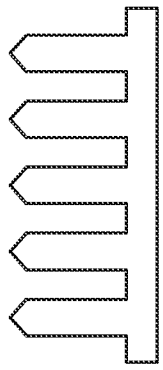
FIG. 9C

APPARATUS AND METHOD FOR IMMUNOMAGNETIC CELL SEPARATION

CROSS-REFERENCE TO RELATED APPLICATIONS

This application is a continuation of U.S. application Ser. No. 15/569,587 filed Oct. 26, 2017, which is a 371 application of International Application No. PCT/US16/31528 filed May 9, 2016, which application claims priority under 35 U.S.C. section 119 (e) to U.S. Provisional Application No. 62/158,845 filed May 8, 2015, 62/174,687 filed Jun. 12, 2015, and 62/213,575 filed Sep. 2, 2015, the entire disclosures of each of the aforementioned applications hereby incorporated by reference.

FIELD OF THE INVENTION

The present invention is directed to a magnetic separation device and relates to a system for large-scale magnetic separation of bioentities.

BACKGROUND OF THE INVENTION

Isolation of biological materials, including eukaryotic and prokaryotic cells, using magnetic labeling is useful in a variety of research and clinical applications. Magnetically labeled bioentities can be rapidly separated from a heterogeneous population by applying an external magnetic field gradient to an aqueous suspension. However, when performing large-scale magnetic separation there are difficulties with obtaining sufficiently enriched target populations. Therefore, it is desirable to develop a system in which magnetic separation can be accomplished with large-volume suspensions in a manner that minimizes manipulation and provides improved recovery of relatively pure target populations.

SUMMARY OF THE INVENTION

The present invention provides a method and apparatus for performing magnetic separations of bioentities that are specifically labeled with magnetic particles.

According to one aspect, the present invention provides a system for magnetic separation of a target bioentity from a fluid suspension of target bioentities and bystander bioentities. The system may include a separation chamber, a magnetic element and a controller for controlling the position and/or orientation of the separation chamber. The separation chamber may include an opening through which the chamber can be filled with a cell suspension having magnetized or magnetizable target bioentities. Additionally, the separation chamber may have a collection surface. The magnetic element includes one or more magnetic elements for applying a magnetic field to the separation chamber to attract the target bioentities. The magnetic field may attract the target bioentities to the collection surface. The controller may be connected with the separation chamber. Additionally, the controller may include a pivot axis for pivoting the separation chamber.

According to another aspect, the present invention provides a method for performing magnetic separation of a bioentity. The method includes the step of providing a fluid suspension in a fluid chamber wherein the fluid suspension comprises a fluid, magnetically labeled bioentities and bystander bioentities. The fluid chamber may be positioned at an angle relative to the horizon. A magnetic field is applied to the fluid chamber to draw the labeled bioentities to a collection surface. The step of applying a magnetic field may include applying a magnetic field so that labeled bioentities are drawn to the collection surface against gravity.

DESCRIPTION OF THE DRAWINGS

The foregoing summary and the following detailed description of the preferred embodiments of the present invention will be best understood when read in conjunction with the appended drawings, in which:

FIG. 5A is a diagrammatic view of a fluid chamber in operative engagement with a magnetic assembly in a first orientation;

FIG. 5B is a diagrammatic view of a fluid chamber in operative engagement with a magnetic assembly in an alternate orientation;

FIG. 5C is a diagrammatic view of a fluid chamber in operative engagement with a magnetic assembly in an alternate orientation;

DETAILED DESCRIPTION OF THE INVENTION

Figure 1:
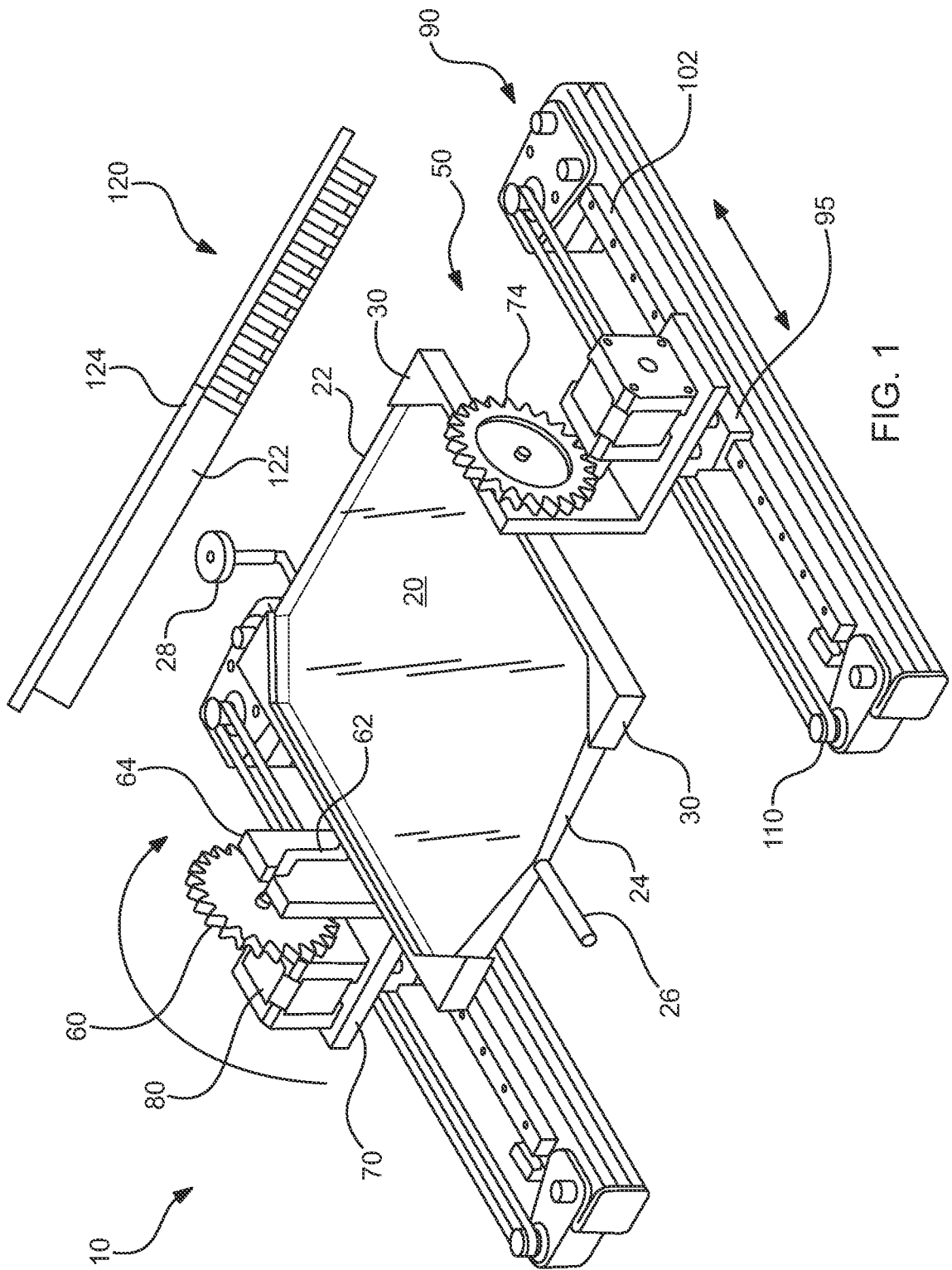
FIG. 1 illustrates an immunomagnetic separation system.

The following definitions will facilitate the understanding of the apparatus and methods used in accordance with the present invention.

The term "medium" as used herein refers to a liquid in which the target bioentity, and other agents used in practicing this invention, is/are maintained in an active form or viable state. A preferred biologically compatible composition is an aqueous solution that is buffered using, e.g. Tris, phosphate or HEPES buffer containing salt ions. Usually the concentration of salt ions will be similar to physiological levels. Biologically compatible media may include stabilizing agents and preservatives.

The term "bioentity" is used herein to refer to a variety of materials of biological or medical interest, including eukaryotic and prokaryotic cells, subcellular organelles, viruses, proteins, nucleic acids, carbohydrates, ligands or complex molecules comprising nucleic acids, proteins, lipids and carbohydrates. A "target bioentity" is separable by the methods described herein. If the target bioentity is a cell, it is also referred to herein as a "target cell."

The term "specifically binding" is used hereinto refer to the interaction between molecules which have particular specificity for each other and which in normal conditions bind to each other in preference to binding to other molecules. Examples of specific binding pairs are antibodies and their cognate epitopes/antigens, ligands (such as hormones, etc.) and receptors, avidin/streptavidin and biotin, lectins and carbohydrates, and complementary nucleotide sequences. These molecules are often expressed on the surface of cells. Various other determinant-specific binding substance combinations are contemplated for use in practicing the methods of this invention and will be apparent to those skilled in the art. Bioentities that are specifically bound to magnetic particles are referred to as "magnetically labeled."

The term "magnetic particle" is used herein to refer to particles that are permanently magnetized and particles that become magnetic only when subjected to a magnetic field. The latter are also referred to herein as "magnetically responsive particles." Materials displaying magnetically responsive behavior are sometimes described as superparamagnetic. However, certain ferromagnetic materials, such as magnetic iron oxide, may be characterized as magnetically responsive when the crystal size is about 30 nm or less in diameter. Magnetically responsive colloidal magnetite may relate to polymer-coated, sub-micron size magnetite particles that behave as true colloids. Small magnetic particles can be useful in analyses involving bio-specific affinity reactions, as they are conveniently coated with bio-functional polymers (e.g., proteins), provide very high surface areas and give reasonable reaction kinetics.

The term "antibody" as used herein, includes immunoglobulins, monoclonal or polyclonal antibodies, immunoreactive immunoglobulin fragments, chimeric antibodies, haptens and antibody fragments, and molecules which are antibody equivalents in that they specifically bind to an epitope on the antigen of interest (e.g. the TCR/CD3 complex or CD28). An antibody may be primatized (e.g., humanized), murine, mouse-human, mouse-primate, or chimeric and may be an intact molecule, a fragment thereof (such as scFv, Fv, Fd, Fab, Fab' and F(ab)'$_2$ fragments), or multimers or aggregates of intact molecules and/or fragments. An antibody may occur in nature or be produced, e.g., by immunization, synthesis or genetic engineering. Preferred antibody fragments for use in T cell expansion are those which are capable of crosslinking their target antigen, e.g., bivalent fragments such as F(ab)'$_2$ fragments. Alternatively, an antibody fragment which does not itself crosslink its target antigen (e.g., a Fab fragment) can be used in conjunction with a secondary antibody which serves to crosslink the antibody fragment, thereby crosslinking the target antigen. A number of anti-human CD3 monoclonal antibodies are commercially available, exemplary are OKT3, prepared from hybridoma cells obtained from the American Type Culture Collection, and the monoclonal antibody G19-4.

The term "enrichment" as used herein refers to increasing the ratio of the target cells to total cells in a biological sample. In cases where peripheral blood is used as the starting materials, red cells are not counted when assessing the extent of enrichment.

The magnetic separation apparatus and methods of the present invention have particular utility in various laboratory and clinical applications. In relevant procedures, a labeling step is utilized in which magnetic particles specifically bind to bioentities of interest that are suspended in a non-magnetic medium. Following this labeling step, the present method also provides for the separation and recovery of the targeted bioentities by applying a magnetic field gradient to the medium.

Separations using magnetic fields are typically gentler processes and preserve the viability of cells. Additionally, high levels of recovery and purity can be achieved by these methods, making them suitable for removal or isolation of rare cells from a mixed population of cells. Such separations include, but are not limited to, enrichment of CD34+ stem cells or immune cells from bone marrow or peripheral blood, isolation of fetal cells from maternal blood, isolation of transfected cells, and removal or isolation of tumor cells from various mixed cell populations. Separations may be accomplished by positive selection or negative depletion, or both, and cells recovered by such separation methods may be utilized for numerous purposes, including further analysis or therapeutic purposes (e.g., re-introduction of cell populations to patients).

There are a number of variables that affect the efficiency with which magnetic separations can be done as well as the recovery and enrichment of magnetically labeled cells. These include such considerations as: the number of cells being separated, the density of targeted determinants present on such cells, the magnetic loading per cell, the non-specific binding of the non-target material, the methodology for magnetically labeling cells, the nature of the vessel, the composition of the vessel surface, and the viscosity of the medium.

For example, when a cell mixture includes red blood cells (RBCs), there are often problems with RBCs becoming entrapped during cell separations. In instances where separations are done from blood, it is customary to first perform a density separation of blood employing a gradient media (such as Ficoll-Paque) to remove RBCs. The method entails expensive reagents, considerable technical skill, and can reduce cell recovery. On the other hand, it is a simpler matter to prepare buffy coats that contain peripheral blood mononuclear cells (PBMC) by centrifugation of blood at appropriate centrifugal forces. However, using a simple buffy coat presents the problem of attempting to recover the entire buffy coat without collecting RBCs. When ferrofluid or other magnetic particle separations are performed on buffy coat preparations, there will invariably be RBC contamination in the recovered fraction. Hence, cell separation protocols that can start with buffy coats and result in an RBC-free product have considerable value in terms of savings (including expensive reagents and technical time). There are also well-known benefits that accrue when fewer manipulations are performed on desired cells. The following description discloses an approach for collecting targeted cells in reasonably ordered layers where bystander cell entrapment is reduced and separation may be accomplished without the re-suspension of the magnetically targeted entities (wash without re-suspension; WWOR).

A magnetic separation device is provided to collect magnetically labeled bioentities by drawing targeted cells, or other bioentities, to one side of a chamber (i.e., onto an inner surface of some vessel). A variety of magnetic gradient devices can be used to accomplish this. In an ideal situation, the magnetic gradient results in the bioentities collecting in uniform layers on the collection surface. Additionally, the chamber containing the magnetically labeled bioentities is positioned such that gradient forces pull the labeled bioentities upward (against gravity) to reduce RBC entrapment and facilitates the removal or washing away of bystander cells entrapped or adhered at the collection surface. Collecting target bioentities on the upper surface of a chamber also facilitates efficient emptying of the contents using gravity and without disrupting target bioentities at the collection surface. Furthermore, if the separation chamber is adequately narrow, the movement of the meniscus of the cell suspension will create a meniscus scrubbing effect that will aid, via shear forces, in washing away non-target cells from the collection surface.

Magnetic Separation Apparatus

Referring now to FIGS. 1-5C, a system for immunomagnetic cell separation is designated generally 10. The system 10 includes a fluid chamber 20 for receiving fluid that includes a cell suspension 150. The cell suspension 150 includes target cells 152 that can be attracted by a magnetic field to separate the target cells from bystander cells 154. Accordingly, the system 10 includes a magnetic assembly 120 for applying a magnetic field to the chamber 20. The system may also include a chamber control assembly 50 for controlling the rotational and longitudinal position of the chamber. Additionally, the chamber control assembly 50 may control the angular orientation of the chamber relative to the magnetic assembly 120. The chamber control assembly may control the distance between the fluid chamber 20 and the magnetic assembly 120.

Referring to FIG. 1, the details of the fluid chamber 20 will be described in greater detail. The fluid chamber 20 may be any of a variety of fluid containers. The walls of the chamber 20 may be formed of rigid or flexible materials. For instance, in the embodiment illustrated in FIG. 1, the chamber comprises a generally planar front wall and a generally planar rear wall. As shown in FIG. 5B, the rear wall is designated 21 and is separated from the front wall by a thickness designated "t". Accordingly, the chamber 20 has a thickness "t". As discussed further below, the rear wall 21 of the fluid chamber is configured to form a collection surface and the target cells 152 are collected onto the collection surface 21 during the cell separation process.

As noted above, the chamber 20 may have rigid walls. For example, the walls may be formed of generally rigid plastic or glass so that the chamber walls do not tend to deform or deflect when rotated or pivoted relative to the horizon. Alternatively, the walls may be formed of one or more flexible walls, such as a container made from plasticized PVC, such as are commonly found in a blood bag.

Figure 2:
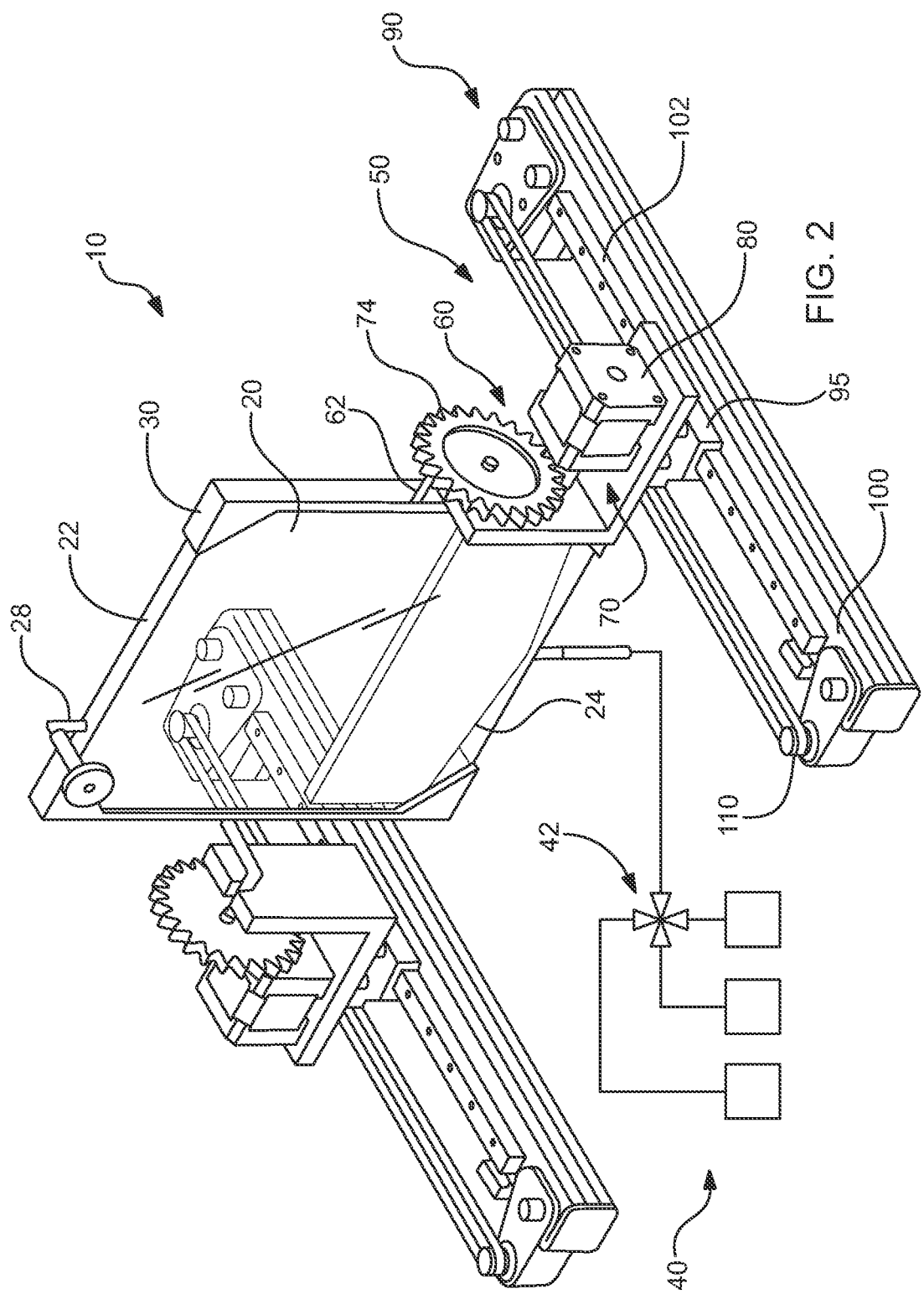
FIG. 2 illustrates elements of the immunomagnetic separation illustrated in FIG. 1.

The fluid chamber 20 has one or more openings or ports for injecting fluid into the chamber or withdrawing fluid from the chamber. In the embodiment illustrated in FIG. 1, the fluid chamber has an upper end designated 22 and a lower end designated 24. The lower end may taper to a point so that fluid will tend to flow toward the point due to gravity when the chamber is at least partially upright. A fill port 26 or opening may be formed in the bottom end of the chamber. For example, as shown in FIG. 1, the fill port 26 may be formed at the tapered point at the lower end of the fluid chamber so that fluid will tend to flow toward the fill port 26 when the chamber is at least partially upright. In addition to the fill port 26, a second port may be formed in the upper end 22 of the fluid chamber. For instance, the second port may comprise a relief opening or valve 28 that permits gas to flow into or out of the fluid chamber. For instance, if fluid is injected into the fluid chamber 20 through the inlet port 26, air in the fluid chamber may escape through the relief opening 28 to prevent a build-up of pressure in the fluid chamber. Similarly, when fluid is drained from the fluid chamber through the fill port 26, air may be pulled into the fluid chamber through relief opening 28. A valve, such as a relief valve, may be connected with the relief opening to control the flow of air into and out of the relief opening. However, in the present instance, a filter is connected to the relief opening to filter air entering the fluid chamber. The filter is configured to impede the flow of liquid out of the fluid chamber when the chamber is disposed in a horizontal orientation as illustrated in FIG. 2.

As mentioned above, and referring to FIG. 2, the system includes a magnetic assembly 120 for applying a magnetic field to the fluid 150 in the fluid chamber. The magnetic assembly includes a magnetic element 122 operable to impart a magnetic field. The magnetic element may be a single magnetic element having a single north pole and a single south pole. Alternatively, the magnetic element 122 may include a plurality of magnetic elements arranged in any of a variety of configurations. Details regarding the types of magnetic elements and the orientation of the magnetic poles as well as the strength of the magnetic elements are discussed in further detail below. Additionally, as discussed further below, the magnetic elements 122 may be mounted on a magnetically conductive element, such as a metal plate 124. The magnetic assembly may be moveable relative to the fluid chamber 20. Alternatively, the magnetic assembly 120 may be mounted onto a stand or bracket that holds the magnetic assembly in a pre-defined position and orientation. The stand or bracket may include a releasable clamping or locking element so that the magnetic element may be releasably retained in a desired position and orientation.

The system 10 further includes a control assembly 50 for controlling the position and orientation of the fluid chamber 20. The fluid chamber 20 may be configured so that the fluid chamber connects directly with the control assembly 50. However, in the embodiment illustrated in FIG. 1, the chamber holder 30 provides a connection between the chamber 20 and the control assembly 50. For example, if the fluid chamber 20 has rigid walls, the chamber holder 30 may include a frame having a plurality of walls that circumscribe the periphery of the fluid chamber. The chamber holder 30 may connect with the fluid chamber so that the fluid chamber rotates and/or translates when the frame holder is rotated or translated. For example, the chamber holder 30 may clamp onto the fluid chamber. Alternatively, the chamber holder 30 may wrap around or overlap the front and rear faces of fluid chamber to hold the fluid chamber. For instance, the chamber holder may form a frame that surrounds the fluid chamber as shown in FIG. 1.

Referring now to FIGS. 1-4, the details of the control assembly 50 will be described in greater detail. The control system 50 is configured to control the angular orientation of the fluid chamber 20 relative to the horizon. The control system may also control the angular orientation of the fluid chamber 20 relative to the magnetic assembly 120. Additionally, the control system 50 may also be configured to control the longitudinal position of the fluid chamber so that the fluid chamber can be translated linearly. In particular, the control system may control the linear position of the fluid chamber relative to the magnetic assembly 120. In this way, the control assembly 150 can control the gap between the fluid chamber 20 and the magnetic assembly 120.

The control assembly 50 includes a rotary control assembly 60 and a linear control assembly 90. The rotary control assembly 60 is configured to control the angular orientation of the fluid chamber 20. The linear control assembly 90 is configured to control that translation or linear position of the fluid chamber.

Figure 3:
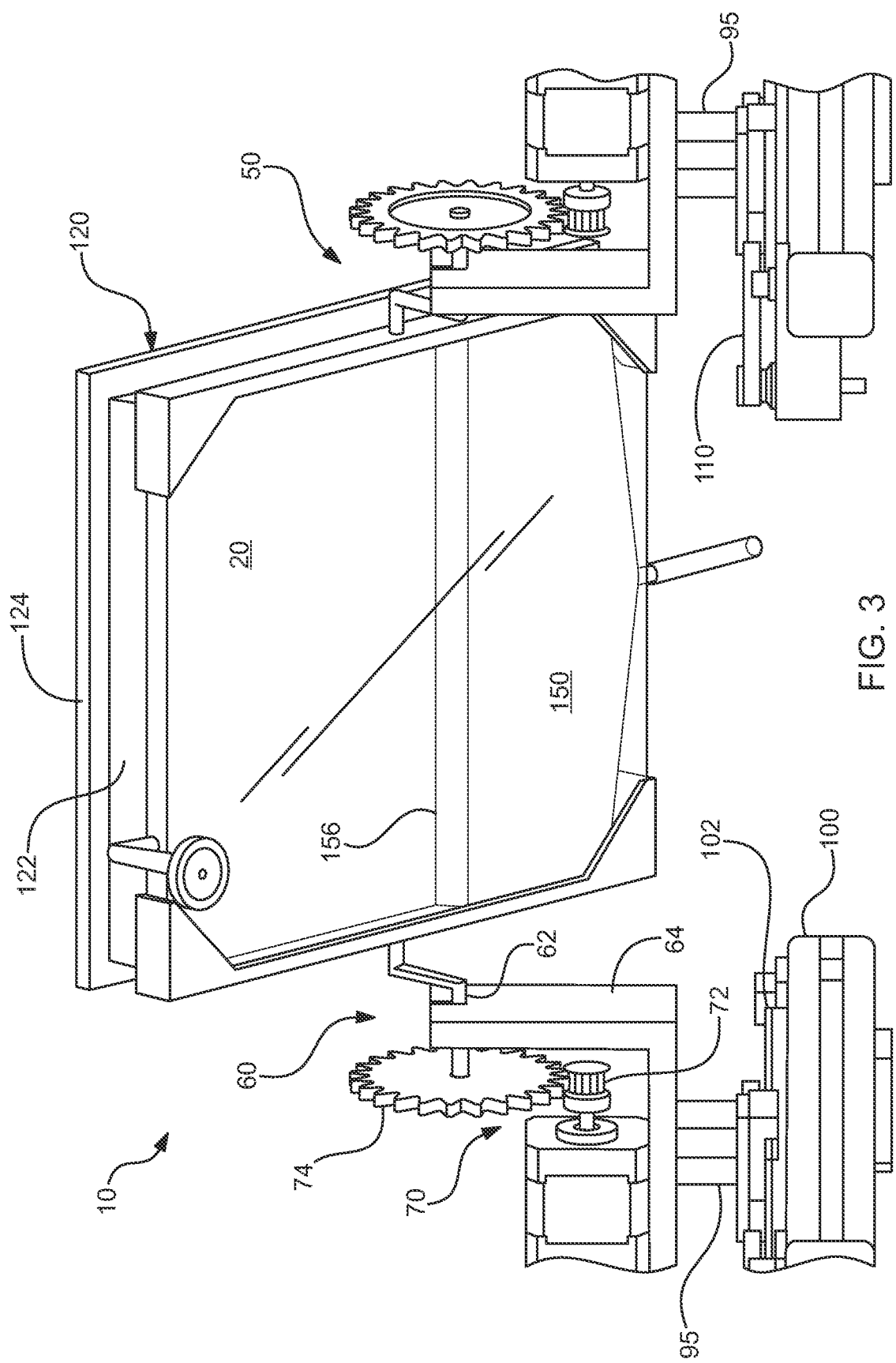
FIG. 3 illustrates the immunomagnetic separation system of FIG. 1, with a fluid chamber illustrated in an alternate orientation.

The rotary control assembly includes a pivot axis 62 connected with the fluid chamber 20 and a support 64 for supporting the pivot axis. The pivot axis 62 may be any of a variety of elements, such as an axle, pivot pin or crank arm. As shown in FIG. 3, in the present instance, the pivot axis comprises an offset crank arm 62. The crank arm 62 includes a pair of parallel legs connected by a transverse connecting rod to form a "Z" or reverse "Z" shape. A first leg of the crank arm is connected with the fluid container 20. For example, in the present instance, the first leg of the crank arm is fixedly connected with the chamber holder 30. Additionally, in the present instance, the second leg of the crank arm 62 is rotationally supported by a mount. For instance, the mount may comprise a yoke 64 having a slot into which the crank arm is retained so that the crank arm can freely rotate relative to the yoke. Alternatively, the yoke 64 may frictionally engage the crank arm to provide sufficient friction to retain the crank arm against rotation. In this way, the yoke may retain the crank arm from rotating in response to the weight of the fluid chamber when the fluid chamber is positioned in a horizontal or angled position (i.e. an orientation in which the weight of the fluid chamber will tend to rotate the fluid chamber about the pivot axis 64).

The pivot axis 62 may be connected with the fluid chamber at any point along the height of the fluid chamber between the lower end 24 and the upper end. As shown in FIGS. 2 & 3, the pivot axis 62 is connected at a mid-point between the upper and lower ends of the fluid chamber. In this way, the fluid chamber is pivotable about an axis that extends about a midpoint of the fluid chamber.

The rotary control 50 may allow the fluid chamber to be manually positioned in a desired orientation and retained in the desired orientation. Alternatively, in the present instance, the rotary controller 50 includes a rotary actuator 70 for controlling the angular orientation of the fluid chamber 20. The rotary actuator 70 may include any of a variety of linear or rotary actuators, including, but not limited to motors, solenoids and hydraulic or pneumatic drive elements. In the present instance, the system includes a motor, such as an electrical motor 80 that drives one of the crank arms 62. The system may include a single motor to drive one of the cranks or as shown in FIG. 3, the system may include a pair of synchronized motors, wherein each motor drives one of the crank arms. The motors are synchronized so that the crank arms 62 are driven synchronously to pivot the fluid chamber 20.

The motors 80 may directly drive the crank arms, however, it may be desirable to include one or more gears to connect the motor 80 with the crank arm 62. As shown in FIG. 3, the rotary actuator may include an input gear 72 connected with the shaft of the motor 80 and an output gear 74 connected with the crank arm. The input gear 72 meshes with the output gear 74 so that the motor drives the crank arm 62 via the gears 72, 74.

The system may further include a linear control assembly 90 for controlling the linear position of the fluid chamber 20. The linear control assembly 90 is operable to translate the fluid chamber 20 along a linear path. For instance, the linear control assembly may include a pair of carriages 95 that ride on longitudinally extending guide rails 102 to guide the displacement of the fluid chamber. Each guide rail 102 is mounted on a base 100 and the two bases are laterally spaced apart from one another. In particular, the bases 100 may be spaced apart wider than the width of the fluid chamber 20 as shown in FIGS. 2 & 3. Each carriage 95 is connected with the rotary actuator control assembly 60 on one side of the fluid chamber so that the carriage displaces the rotary actuator along the linear path. As shown in FIG. 2, the carriage 90 comprises a block having a longitudinally extending slot configured to mate with the guide rail 102 so that the carriage straddles the guide rail.

The linear control assembly 90 may be configured to provide a frictional resistance so that the carriage resists linear displacement once the assembly is moved into a particular location along the length of the guide rail. Alternatively, as shown in FIG. 2, the linear control assembly 90 may include a linear actuator 110 operable to drive the carriage 95 along the guide rail so that the actuator controls the position of the carriage along the guide rail. In this way, the linear actuator controls the linear position of the fluid chamber. Specifically, in the embodiment illustrated in FIGS. 1-4, the linear actuator 110 controls the horizontal displacement of the fluid chamber. The linear actuator 110 may be any of a variety of actuators, including, but not limited to motors, solenoids and hydraulic or pneumatic elements. In the present instance, the linear actuator includes a drive belt that drives the carriage 95 along the guide rail 102.

Referring again to FIG. 1, the system 10 may also include a fluid control assembly 40 for controlling the flow of fluid to and from the fluid chamber. The fluid control assembly may include a plurality of fluid reservoirs. Each reservoir is configured to receive fluid and each reservoir is in fluid communication with the fluid chamber 20 so that fluid can either flow from the reservoir to the fluid chamber or fluid can flow from the fluid chamber to the reservoir. For instance, the fluid control assembly 40 may include a plurality of reservoirs for receiving fluids, such as cell suspension, immunomagnetic reagent (e.g. ferrofluid) and a buffer solution. Additionally, a reservoir can be provided for receiving the target cells to be collected from the fluid chamber 20. For instance, a fluid line may be connected with the inlet port 26. The fluid line may be connected with a multi-position valve or a selector valve 42 to control which of the reservoirs is in fluid communication with the fluid chamber 20. In particular, the valve is configured so that only one of the reservoirs is in fluid communication with the fluid chamber at any time. Additionally, the valve may stop the flow of fluid between the reservoirs and the fluid chamber so that no fluid flows into or out of the fluid chambers through the fill port 26. A drive element, such as a pump, may be provided to pump fluid from one or more of the reservoirs into the fluid chamber 20. Alternatively, the reservoirs may be positioned so that gravity drives fluid from the reservoirs into the fluid chamber 20.

Magnetic Assembly

A magnet is used in the system to subject the contents of the chamber to a magnetic gradient. The magnet may be a single magnet or a magnetic array. The magnet may have a generally planar surface. Additionally, the magnet may have a face having a surface area large enough to subject a substantial majority of the chamber to a magnetic gradient. When the magnet contacts or is in close proximity to the chamber, magnetically labeled bioentities accumulate on an inner surface of the chamber, which forms a collection surface. In some embodiments, the magnet is positioned near the base and the chamber can be moved linearly so that it contacts or is in close proximity to the magnet. Accordingly, such magnet may be in a fixed, angled position or be capable of rotating at an angle substantially the same as the chamber.

Figure 6B:
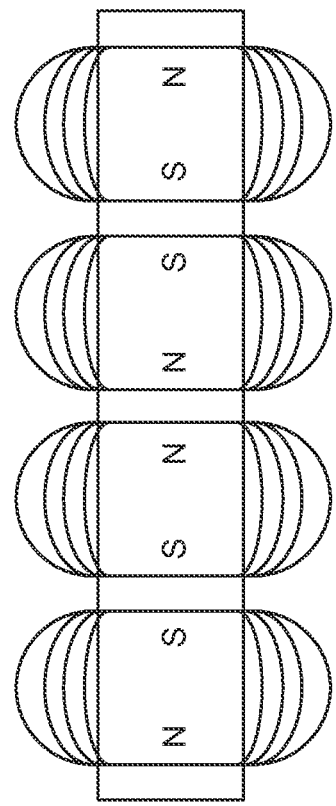
FIG. 6B is a diagrammatic view of a second arrangement of magnetic elements for a magnetic assembly of the immunomagnetic separation system of FIG. 1.
Figure 6A:
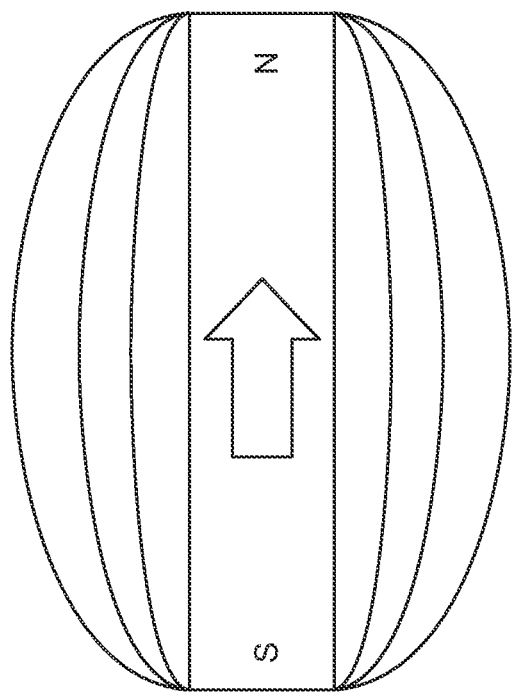
FIG. 6A is a diagrammatic view of a first arrangement of magnetic elements for a magnetic assembly of the immunomagnetic separation system of FIG. 1.
Figure 6C:
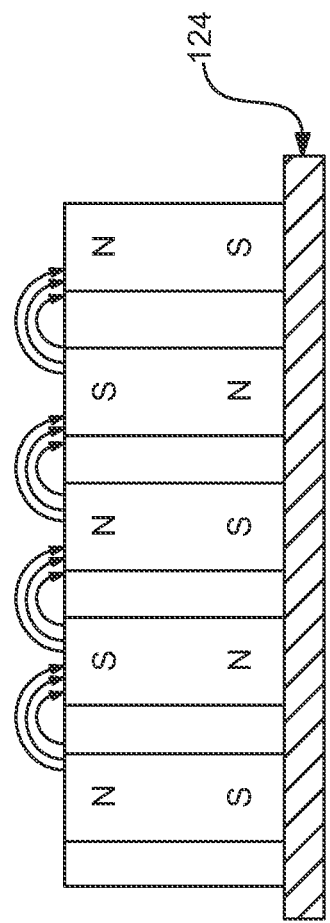
FIG. 6C is a diagrammatic view of a third arrangement of magnetic elements for a magnetic assembly of the immunomagnetic separation system of FIG. 1.

The magnet used in the system 10 may be arranged and/or configured to reduce the likelihood of bioentities collecting in piles on collection surfaces. FIGS. 5A-5C depict three alternate magnets or magnetic arrays that can be used to create magnetic field gradient forces directed to a planar surface. FIG. 6A shows an array of block magnets where the polarities are parallel to the plane in which collection occurs and where the block magnets are arranged with like poles adjacent to one another (i.e., north-to-north and south-to-south). The circuits formed by such an array bulge out to the sides of the magnetic array and create gradients towards the magnet face, particularly near magnet-magnet interfaces. This magnetic array layout is operable to collect large, highly magnetic particles, however, the arrangement may result in significant piling of bioentities. FIG. 6B shows a cross-section of a rectangular block magnet which depicts an alternate arrangement of magnets for creating a magnetic gradient directed toward a plane. In this case, the polarity, shown by an arrow, is in the long dimension of the magnet. Accordingly, the field lines traversing from north to south above and below the planar surface create a gradient force directed to the surface. Consequently, such gradients may be limited in strength and reach when compared with the arrangement in FIG. 6A. FIG. 6C shows another array for creating a gradient magnetic force directed toward a surface where the magnetic array is composed of block magnets mounted on a magnetically conductive plate. The polarity is perpendicular to the magnetically conductive plate, and the polarity of the magnetic blocks alternates. Such a magnetic array collects magnetic entities in localized regions of high magnetic gradient.

In addition, the magnetic array depicted in FIG. 6C can create strong gradients that can be varied with respect to intensity and field extension (i.e., "reach") depending on the dimensions, pole face shapes, and spacing of such magnets. FIGS. 8A-8D and 9A-9D illustrate the results of computational analysis for four magnet geometries that are primarily of rectangular cross-section and configured such as those in FIG. 6C, but where the pole face for each magnet in the array is square (FIGS. 8A & 9A), rounded (FIGS. 8B & 9B), triangular (FIGS. 8C & 9C), or gothic steeple-like (FIGS. 8D and 9D). Computations using finite element analysis were made for these different pole faces as a function of spacing between magnets.

Figure 8A:
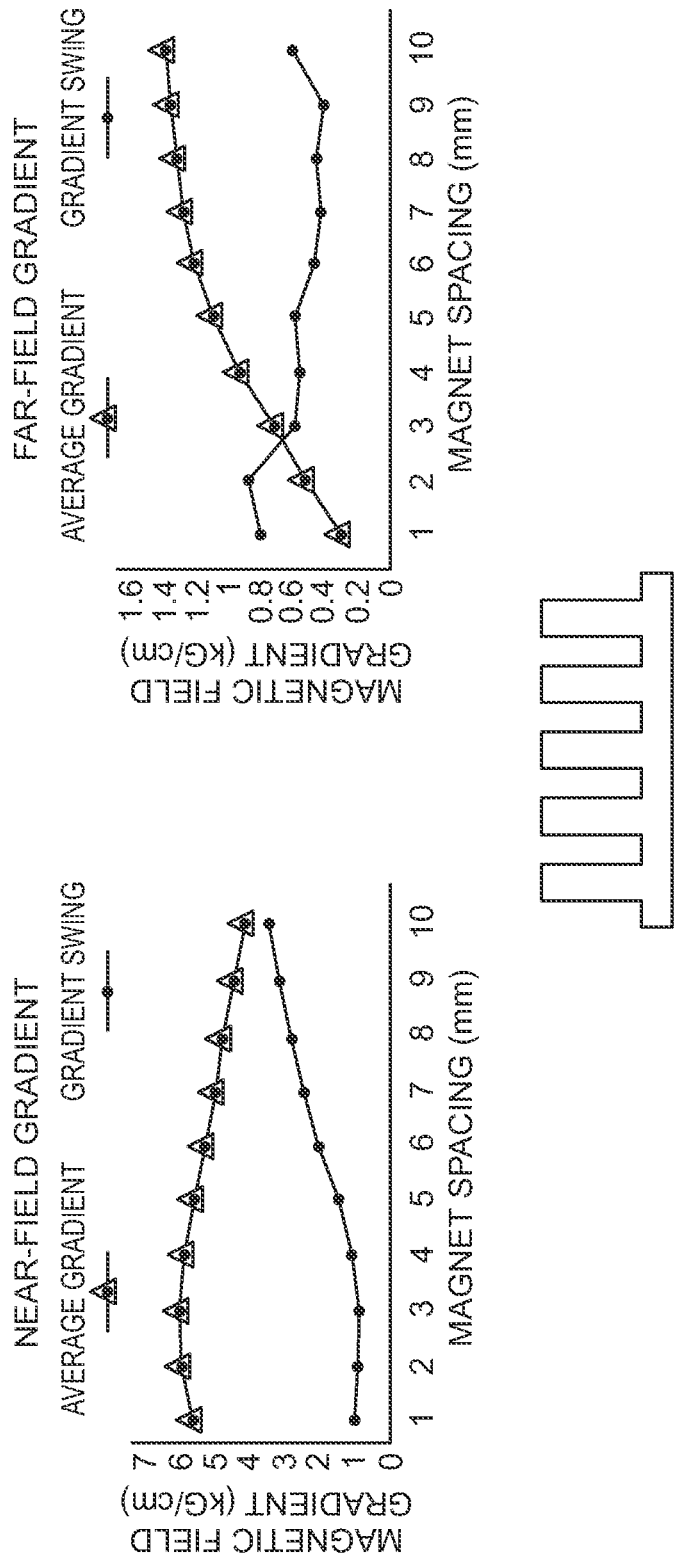
FIG. 8A-D are schematic views and graphs analyzing the magnetic gradient of four magnet configurations.
Figure 8B:
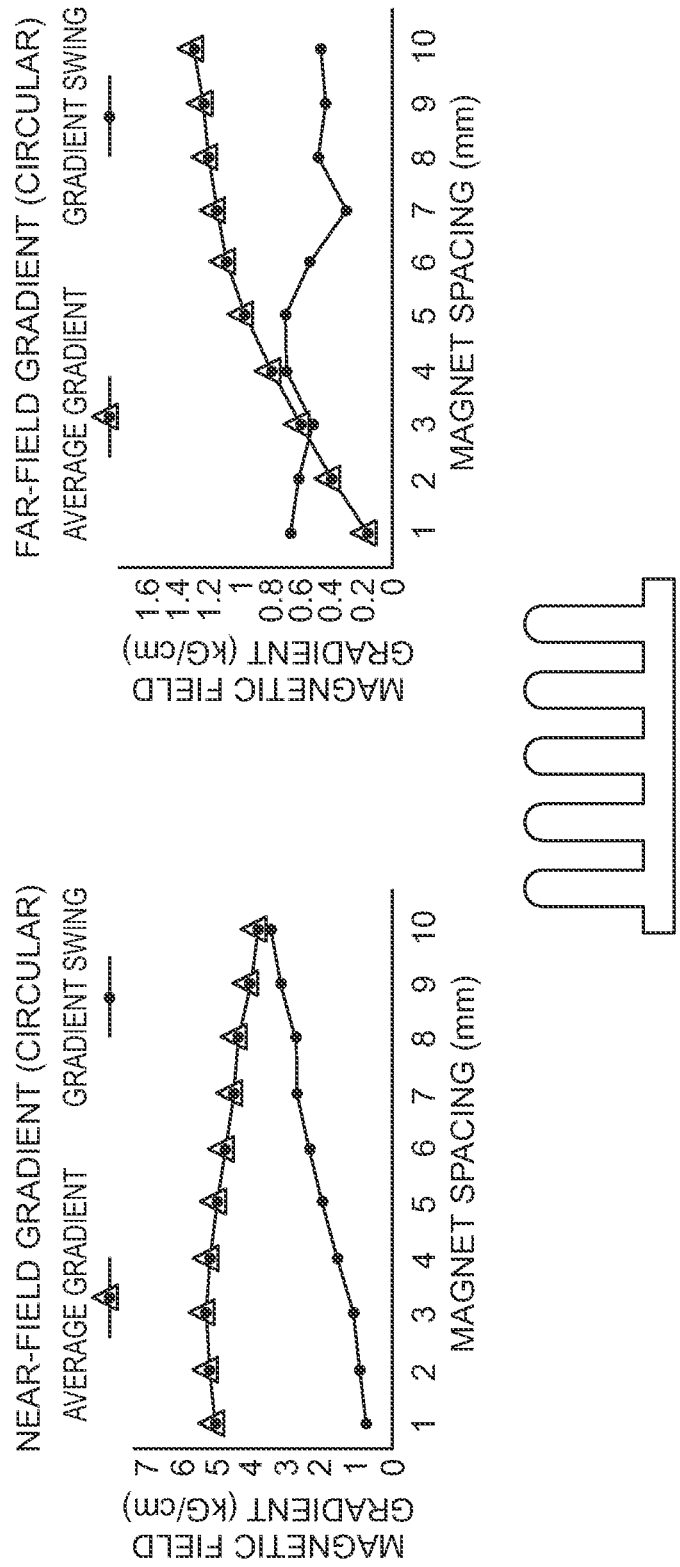
Figure 9A:
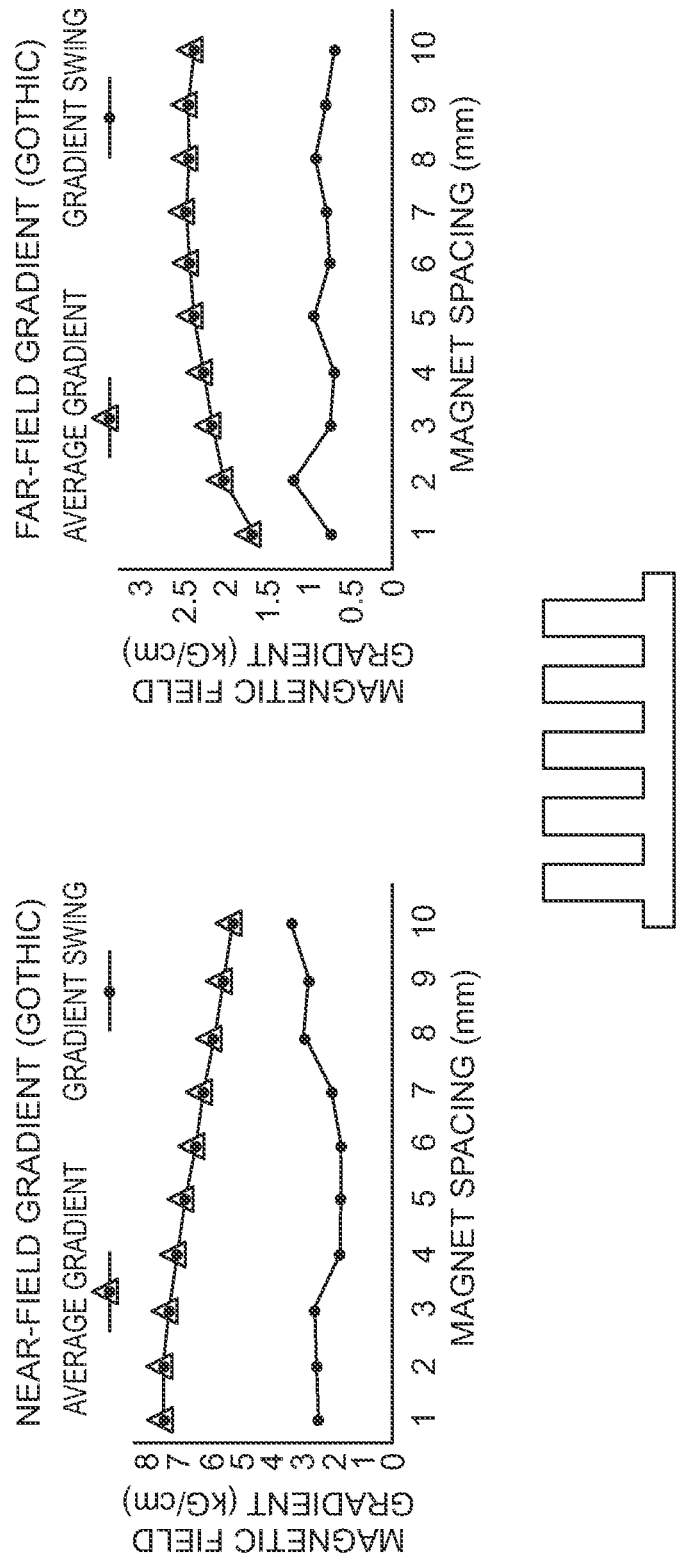
FIG. 9 A-D are schematic views and graphs analyzing the magnetic gradient of four alternate magnet configurations.
Figure 9B:
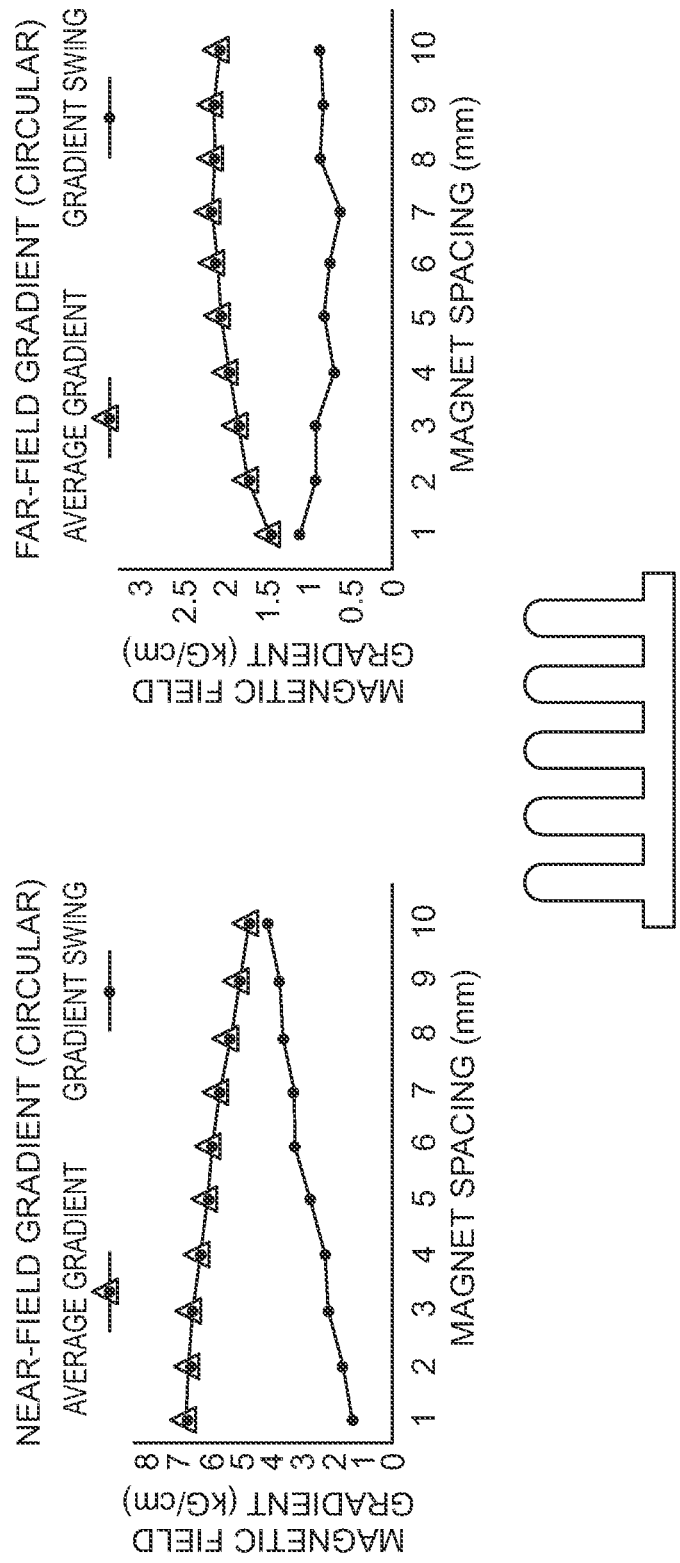
Figure 9D:
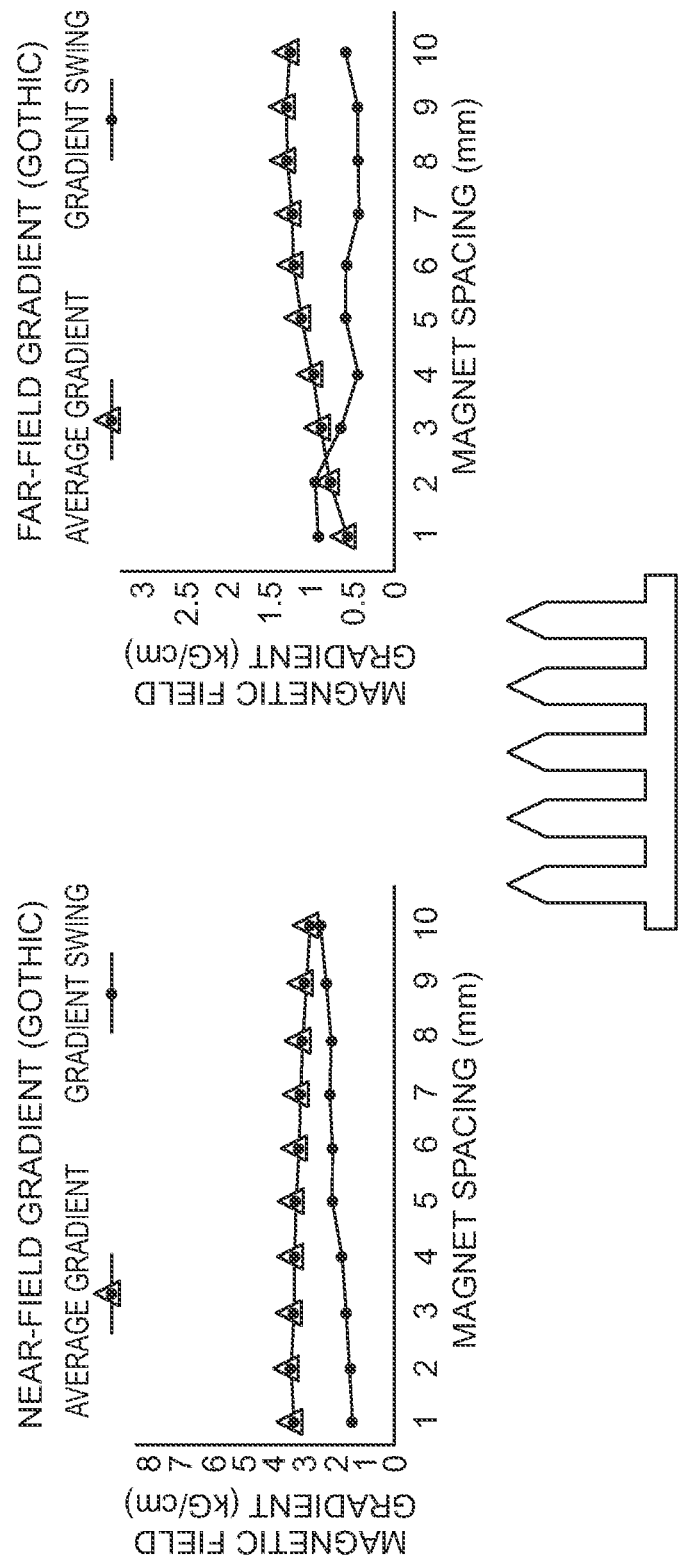

FIG. 8A shows the average magnetic field gradient (relative to the magnet face) consisting of square pole face magnets as a function of magnet spacing and the difference between the maximum (typically centered above the magnets) and the minimum (typically centered between the magnets) in those values (i.e., the swing) as a function of magnet spacing. As indicated by the top curve of that FIG. 8A, it can be seen that the average magnetic field gradient goes through a maximum as spacing between the magnets varies from 1 to 10 mm (note that these individual magnets are 5 mm in width and 20 mm in height, and the calculations are based on using N52-grade NeFeB magnets). The bottom curve of that panel shows the swing (i.e., the variation in the gradient moving across the magnetic face of each array) in those values for each magnet spacing arrangement (1-10 mm). These variations (not shown) look similar to sine waves with periods corresponding to the number of individual magnets used for each magnetic array. For example, for these 5 mm-wide block magnets spaced at 1 mm, FIG. 8A shows the average gradient across the planar surface is approximately 5.6 kG/cm and the swing of that gradient (taken from the lower curve) is approximately 1.0 kG/cm. For magnets spaced 10 mm apart, the average gradient is approximately 4.0 kG/cm, but the swing is approximately 3.4 kG/cm. Thus the 1 mm spacing has maximum gradients of approximately 6.0 kG/cm, whereas with the 10 mm spacing, the maximum gradients are approximately 5.8 kG/cm. Since these "near-field" gradients represent holding power of magnetically attracted entities, it would be evident that high gradients are desirable. On the other hand, to obtain more uniform collection across such surfaces, lower gradient swing results in less significant localization of collected materials. The upper curve of FIG. 8A shows that the average gradient goes through a maximum when magnet blocks are spaced between 2 and 3 mm, and the swing is flat from 1 to 3 mm spacing and begins to rise at 4 mm. Since it is desirable from a cost perspective to use as few magnets as possible, this analysis indicates that for this magnet arrangement, a spacing of 3 mm will result in minimum localization with maximum holding strength. A second consideration is magnetic reach (i.e., the ability to pull magnetic entities farther from the magnet face into the high-gradient region where they can be held magnetically. FIG. 8B shows the results of gradients calculated from 12 mm to 7 mm (relative to the magnet face). The upper curve shows that the average magnetic far-field gradient (or reach), improves as the spacing increases. The lower curve of FIG. 8B shows the swing in those values, which are relatively small considering the scale. As indicated by these curves, the far-field gradient at 3-4 mm spacing is between 0.5 kG/cm and 1.0 kG/cm when the swing is considered. From experiments with ferrofluid and cells, it has been determined that such gradients are adequate to move magnetically labeled cells and, accordingly, allow the use of a chamber with a thickness/depth that extends 12 mm from the magnet face.

Figure 8C:
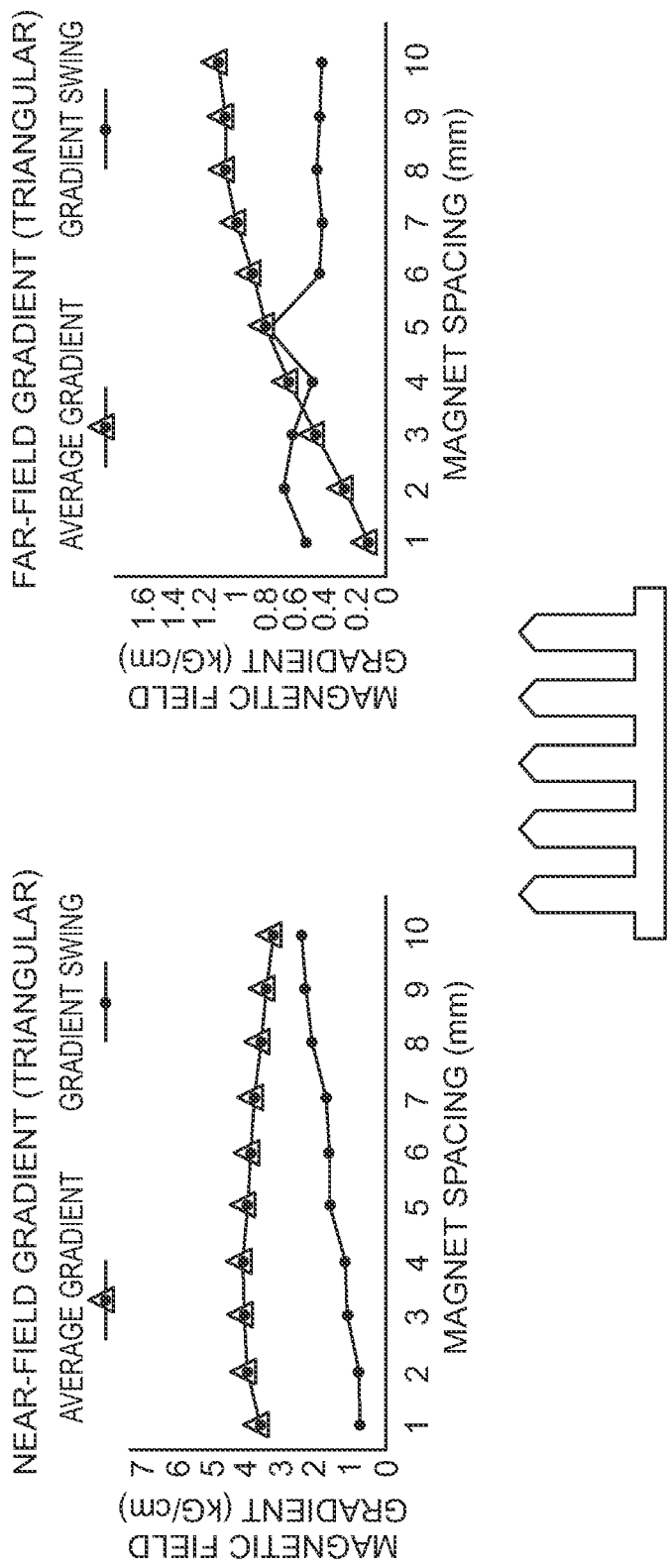
Figure 8D:
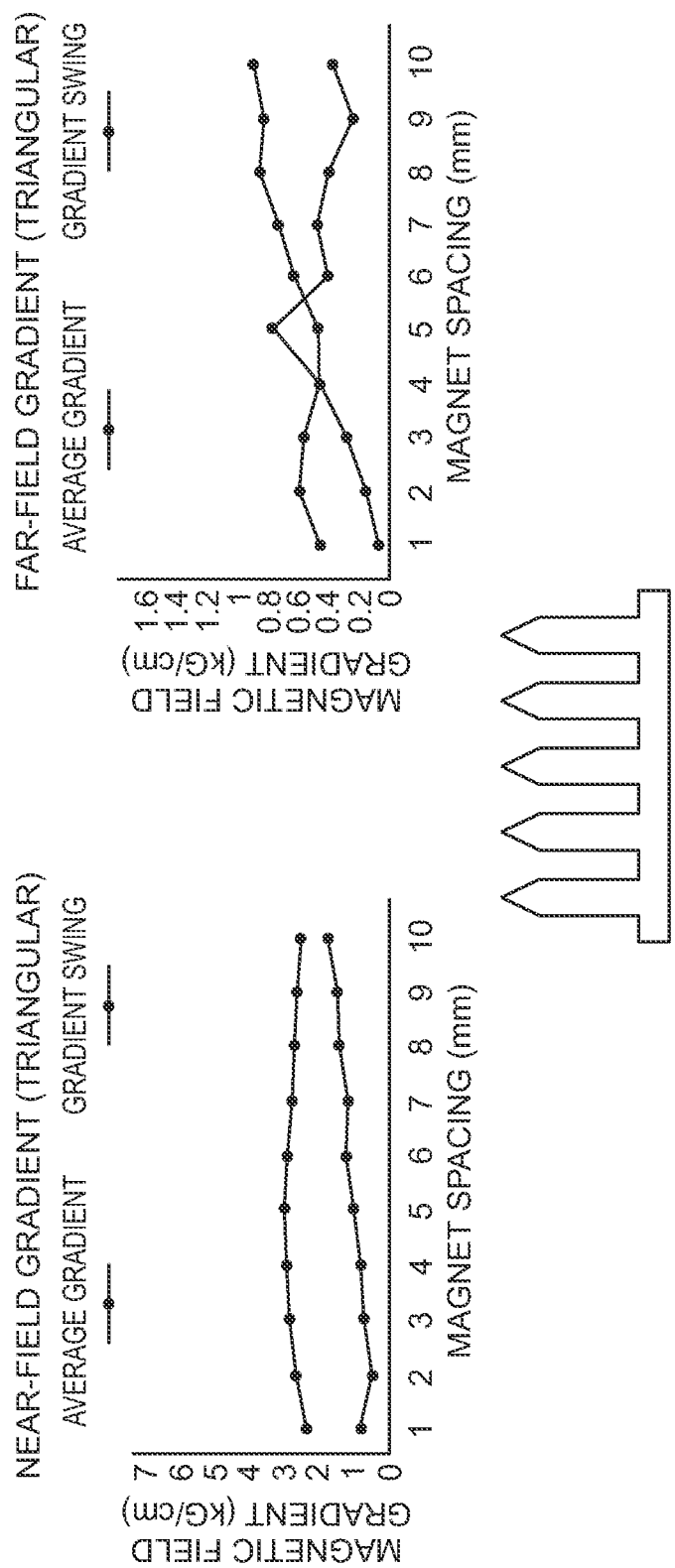

Likewise, FIGS. 8B-8D depict computational results for 5 mm wide magnets that have pole faces that are circular, triangular and gothic steeple-like. Focusing on the near-field swings (the lower curves of the upper panels), with the exception of the 2 mm spacing in FIG. 8D which is approximately 0.5 kG/cm, varying the pole face shapes does little to improve upon the field uniformity from the rectangular pole face shape with 3-4 mm spacing. Moreover, the holding power generated by the gothic steeple-like pole faces of FIG. 8D is substantially reduced.

FIGS. 9A-9D illustrate similar computational analysis for wider magnets (10 mm) to determine the effects of greater magnetic mass on gradient parameters. In both cases, calculations were made using block magnets 20 mm in length. For such magnets, flux density at the poles does not increase substantially once the magnetic length reaches approximately 13 mm; thus, these calculations were made using magnets that produce nearly maximum flux. The analyses were performed for the same pole face shapes as shown for the 5 mm-wide magnets. The results for magnetic "near-field" and "far-field" gradients are depicted in FIG. 9A-9D. For example, in FIG. 9A, the upper curve indicates average values of the near-field gradient, while the lower curve of that panel indicates the swing as a function of spacing for square pole face magnets. The maximum near-field gradients are approximately 7.4 kG/cm with a swing of approximately 2.4 kG/cm. That is substantially higher than the 5 mm-wide magnets (FIG. 8A), where maximum values are approximately 5.9 kG/cm with swings of approximately 0.9 kG/cm. Therefore, the holding force of the wider magnets is substantially higher (ca. 25%), but the swing percentage change is also higher (32% for 10 mm-wide magnets vs. 15% for 5 mm-wide magnets). Accordingly, the narrower magnets have merit if minimization of cell localization upon collection is of primary concern. On the other hand, the wider magnets have a substantially greater reach as evidenced by the far-field gradient values (upper curves of FIGS. 9A-9D). For example, in FIG. 9B, the reach approaches its limit at approximately 2.4 kG/cm (swing of 0.8 kG/cm), whereas the maximum reach for the 5 mm magnets is about 1.4 kG/cm (swing of 0.6 kG/cm). Thus the wider magnets produce gradients that have greater holding power and reach, but wider swings that will lead to more severe cell localization as compared to the narrower magnets.

From the foregoing, parameters for optimal magnetic collection on a planar surface (defined here as minimal localization of magnetically collected entities) can be predicted by computational analysis. By constructing magnetic arrays of the types used for these computations, it has been shown that magnetic collection patterns correlate with those predicted by these analyses. As shown above, narrower magnets confer an advantage for achieving uniform collection when the holding force and reach are adequate. For example, in a chamber as deep as 12 mm, it is possible to pull magnetically labeled bioentities to a collection surface 2 mm away from the planar surface of 5 mm wide magnets spaced 3-4 mm apart, achieve reasonably uniform cell collection, and have a reach such that all cells within the chamber are magnetically retrievable. For the 10 mm-wide magnets, optimal spacing of magnets is also approximately 3-5 mm to achieve a strong holding force and adequate reach in such a chamber. Consequently, for deeper chambers, magnets with widths of 10 mm or greater would be desirable.

An exemplary plate-type magnetic device can magnetically collect labeled target cells when the magnetic elements were as far as 11 mm from the magnetic face. Collection vessels used with this system can be any of a variety of shapes and sizes, including but not limited to square or rectangular cross section. One advantage of using square or rectangular collection vessels in concert with a magnet that draws target bioentities to one side of a chamber is that the collection surface is rectilinear. Accordingly, cells collect on a flat surface as opposed to on a curved surface as they would if the chamber was a tube. A flat collection surface allows for the bioentities to collect evenly when using appropriate gradient devices.

Figure 7:
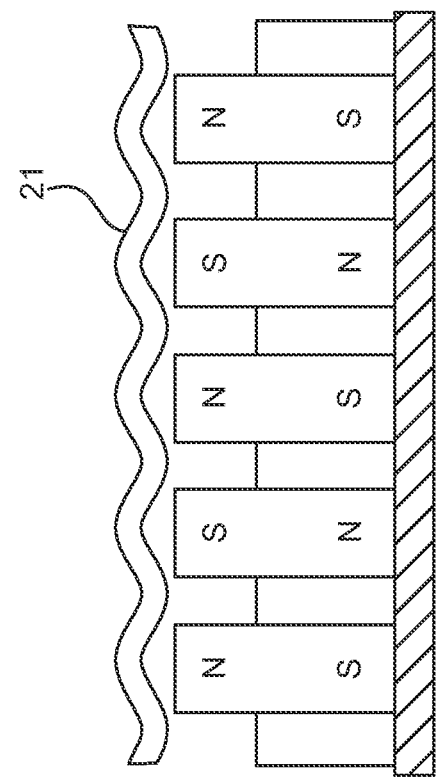
FIG. 7 is a diagrammatic view of a fourth arrangement of magnetic elements for a magnetic assembly in combination with an alternate fluid chamber.

In addition to using a planar magnet, there are alternative means to achieve uniform collection. For example, by contouring the bottom of the chamber to match the periodicity of the magnetic gradient, bioentities at any point on the contoured collection surface can be exposed to the same magnetic gradient. For instance, referring to FIG. 7, the collection surface of the fluid chamber is contoured and rests atop block magnets and recessed spacers configured in an alternating fashion. Although the collection surface is uneven, the magnetic gradient is constant at each point on the surface. Thus by appropriate shaping of a contoured collection surface, uniformity of bioentity collection and holding force can be achieved.

There are clearly many angles for positioning the magnet and chamber in the separation system. Some of these arrangements result in differential forces on magnetically labeled bioentities during the separation, that is, where the magnetic and gravitational forces are at an angle and/or at least partially opposing. In the case of batch separations, as opposed to flow-through separation chambers, it can be difficult to wash and recover collected targeted bioentities when the chamber is positioned horizontally and target bioentities are pulled upwards as in FIG. 5B. On the other hand, as depicted in FIG. 5C, placing the magnet on some angle greater than 0°, with an angle near 45° being illustrated, where the magnet is situated above the chamber, allows for the filling or draining of the chamber through a bottom port while minimally disrupting target bioentities accumulated at the collection surface. The closer the angle is to vertical, the greater the volume that can be placed in the vessel. FIGS. 5A-5C show cross sections of simple rectangular separation chambers paired with magnets in three different orientations and where collection surfaces for each vessel are on the bottom the chamber (FIG. 5A), the top of the chamber (FIG. 5B), or, where the magnet and chamber are placed on an angle, depicted here as a 45° angle, accumulation of magnetic bioentities occurs on a tilted 'ceiling' which is also at a 45° angle relative to horizontal (FIG. 5C).

Method of Performing Magnetic Separation

The system described above may be used for a variety of applications that entail magnetic separation of biological material. The system is particularly suited for isolating cells from a suspension. In the following example, a process is described for the separation of cells from a leukapheresis product; however, the system may be adapted to a variety of separation procedures for isolating magnetically labeled bioentities.

Configured as described above, the system 10 can be used to prepare a cell suspension for immunomagnetic cell separation. In particular, the system can be used to label the target cells 152 by loading the target cells with magnetic or magnetizable elements. Specifically, the system may label target cells 152 by injecting a quantity of cell suspension into the fluid chamber. A quantity of magnetic or magnetizable elements is then injected into the fluid chamber 20. For instance, a quantity of ferrofluid may be injected into the fluid chamber 20. Alternatively, the magnetic or magnetizable elements may be first injected into the fluid chamber 20, followed by addition of a quantity of cell suspension. As shown in FIG. 1, the cell suspension and ferrofluid are in the fluid chamber such that the suspension has a relatively high cell concentration. The fluid chamber 20 may be in a generally vertical or upright orientation when the cell suspension and ferrofluid is injected into the fluid chamber 20 as shown in FIG. 1. For example, 80 mL of platelet-free leukapheresis product (ca. $1.2 \times 10^8$ cells/mL) and 20 mL of ferrofluid may be injected into the fluid chamber 20. The mixture can be left to incubate so that the target cells are labeled. Optionally, the chamber control assembly may control the angular or lateral position of the fluid chamber to agitate the fluid in the fluid chamber to improve the incubation. For instance, the linear actuator can drive the fluid chamber forwardly and rearwardly along the guide rail to shake the fluid chamber back and forth. Similarly, the rotary actuator can pivot the fluid chamber clockwise and counterclockwise to agitate the fluid mixture in the fluid chamber. Alternatively, rather than the linear and rotary actuators agitating the fluid mixture, the fluid chamber control assembly can be used to manually move the fluid chamber laterally and/or angularly to agitate the mixture.

Rather than shaking or agitating the fluid to mix the fluid mixture, the fluid chamber may be moved toward and away from the magnetic assembly 120 to enhance the labeling process. In particular, the chamber control assembly 50 may control the position and/or angular orientation of the fluid chamber relative to the magnetic element. For example, the linear control assembly may be actuated (either manually or by linear actuator 110) to drive the fluid chamber toward the magnetic assembly 120 so that the magnetic field from the magnetic element is applied to the fluid mixture. By moving the fluid chamber toward and away from the magnetic field, the magnetic gradient is controlled. In particular, the magnetic gradient applied to the cell suspension increases and decreases. By varying the magnetic gradient applied to the mixture, the magnetic field redistributes the ferrofluid in the mixture. By redistributing or translating the ferrofluid, collisions with target cells are increased, thereby enhancing magnetic loading of the target cells. Accordingly, by moving the cell suspension relative to the magnetic element to vary the magnetic gradient applied to the cell suspension, the process of target cell labeling is accomplished more quickly than if the magnetic gradient applied to the cell mixture is not varied over time.

As discussed above, the system 10 can be used to label target cells. Additionally, the system 10 can be used to separate target cells 152 from a bystander cells in a cell suspension. A volume of cell suspension is injected into the fluid chamber. In particular, the cell suspension may be a mixture that has been processed according to the incubation process described above. In such an instance, the cell suspension is already in the fluid chamber (i.e. the cell suspension does not need to be drained from the fluid chamber after the incubation process). Alternatively, the cell suspension may be incubated separately and injected into the fluid chamber 20 to separate the target cells 152 from the bystander cells. In order to minimize cell entrapment it may be desirable to dilute the cell concentration relative to the cell concentration during the incubation process. For instance, during the incubation process described above, the cell suspension has a concentration of approximately $1.2 \times 10^8$ cells/mL. Accordingly, it may be desirable to add a volume of buffer fluid to reduce the cell concentration. For example, it may be desirable to add sufficient buffer to the solution to increase the total volume by 100% or more. It may also be desirable to increase the total volume by over 200%. In some applications, it may be desirable to increase the total volume by over 300%. For example, in the present instance, the total volume of the cell suspension 150 may be increased to 300 mL by adding 200 mL of buffer. As a result, the cell concentration may be reduced to approximately $3 \times 10^7$ cells/mL.

As shown in FIG. 1, the volume of cell suspension 150 during the incubation process is significantly less than the total volume of the fluid chamber. More specifically, the cell suspension is less than half the volume of the fluid chamber. In particular, the cell suspension is less than one third of the volume of the fluid chamber. In this way, when the fluid chamber is oriented in a general vertical orientation as shown in FIG. 1, the upper surface of the fluid suspension forms a meniscus 156 that is substantially below the upper end 22 of the fluid chamber 20. In the embodiment illustrated in FIG. 1, the meniscus is below the midpoint of the height of the fluid chamber 20.

Figure 4:
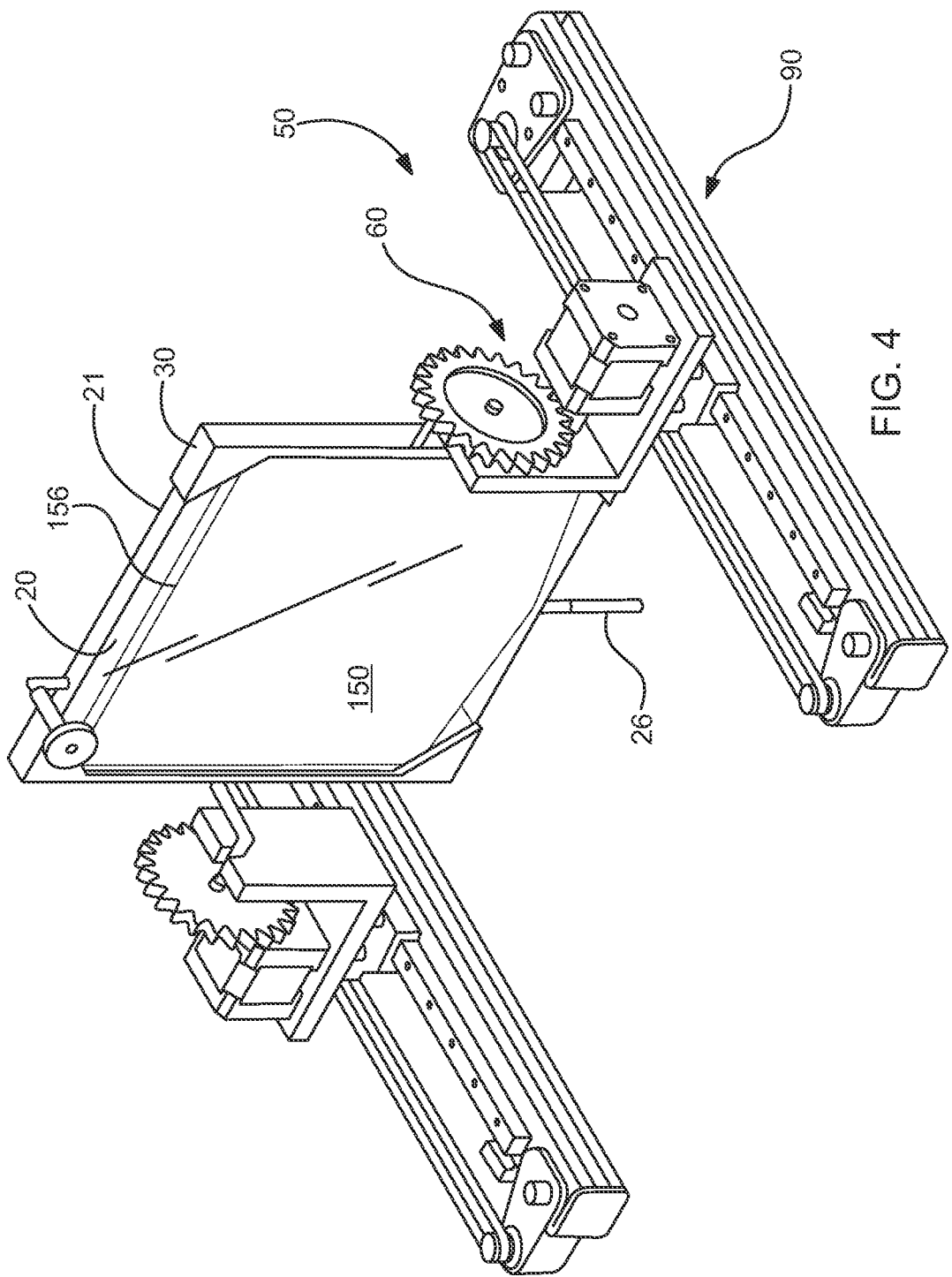
FIG. 4 illustrates the elements of the immunomagnetic separation system illustrated in FIG. 2, after a step of diluting the cell suspension.

Referring to FIG. 4, the volume of the fluid chamber 20 may be greater than the volume of the cell suspension after the suspension is diluted to reduce the cell concentration. In particular, after the step of adding buffer, the meniscus 156 of the cell suspension is below the upper end 22 of the fluid chamber. Specifically, an air pocket or gap is formed between the meniscus 156 and the upper end of the fluid chamber 22.

Although the volume of the fluid chamber is greater than the volume of the cell suspension, it may be desirable to limit the volume of the air pocket so that the cell suspension overlaps a substantial majority of the area of the collection surface 21 of the fluid chamber 20. In particular, the volume of cell suspension is sufficient to cover over 50% of the surface area of the collection surface 21 when the fluid chamber is disposed in the orientation used during the magnetic separation step. More specifically, the volume of cell suspension is sufficient to cover over 60% of the surface area of the collection surface 21 when the fluid chamber is disposed in the orientation used during the magnetic separation step. Still further, the volume of cell suspension may be sufficient to cover over 70% of the surface area of the collection surface 21 when the fluid chamber is disposed in the orientation used during the magnetic separation step. Further yet, the volume of cell suspension may be sufficient to cover over 80% of the surface area of the collection surface 21 when the fluid chamber is disposed in the orientation used during the magnetic separation step. In particular, the volume of cell suspension may be sufficient to cover over 90% of the surface area of the collection surface 21 when the fluid chamber is disposed in the orientation used during the magnetic separation step.

As shown in FIG. 4, the fluid chamber 20 may be rotated into a substantially vertical orientation during the step of adding buffer to the cell suspension. The fluid chamber is then brought into operative engagement with the magnetic element. In particular, the fluid chamber is moved relative to the magnetic element 120 so that the magnetic element applies a magnetic gradient through the cell suspension in the fluid chamber. This may be accomplished by moving the magnetic assembly 120 toward the fluid chamber 20. However, in the present instance, the chamber control assembly 50 is operated to displace the fluid chamber 20 toward the magnetic assembly. In particular, the linear actuator 110 is actuated to drive the fluid chamber 20 toward the magnetic assembly 120. Additionally, the chamber control assembly 50 may be operated to rotate the fluid chamber 20. In particular, the rotary actuator 70 may be operated by driving the motor 80 to rotate the fluid chamber 20. Specifically, the rotary actuator 70 may rotate the fluid chamber until the fluid chamber is aligned with the magnetic assembly 120. For example, the rotary actuator 70 may rotate the fluid chamber until the collection surface 21 is substantially parallel with the magnetic assembly. In this way, the position and orientation of the fluid chamber is manipulated by the chamber control assembly 50 so that the fluid chamber is brought into operative engagement with the magnetic assembly 120. In particular, the fluid chamber 20 is positioned so that the collection face 21 is adjacent to or abutting the magnetic assembly as shown in FIG. 3 and FIGS. 5A-5C.

When the fluid chamber is brought into operative engagement with the magnetic assembly 120, the magnetic assembly applies a magnetic field to the cell suspension 150 that draws the target cells toward the collection surface 21 of the fluid chamber. Specifically, the magnetic field applied to the cell suspension attracts the target cells that have been labeled. In addition to attracting the target cells 152 to the collection surface 21, the magnetic assembly retains the target cells on the collection surface. After the magnetic field is applied to the cell suspension, the fluid suspension 150 may be drained from the fluid chamber while the fluid chamber remains in operative engagement with the magnetic assembly. In this way, the bystander cells are drained from the fluid chamber while the target cells remain on the collection surface 21, held in place by the magnetic force from the magnetic assembly 120.

After the step of draining the cell suspension, there may be some bystander cells 154 entrapped with the target cells 152 on the collection surface 21. The bystander cells 154 may be scrubbed from the collection surface 21 by filling the fluid chamber 20 with buffer fluid. As the buffer is injected or pumped into the fluid chamber, the meniscus of the fluid agitates the cells on the collection surface. The agitation or scrubbing provides sufficient force to displace the bystander cells away from the collection surface so that the bystander cells fall away from the collection surface. The step of scrubbing can be repeated by draining and re-filling the fluid chamber with buffer as many times as necessary to separate the bystander cells from the target cells that are collected on the collection surface. In the present instance, the fluid chamber remains in operative engagement with the magnetic assembly 120 during the step(s) of scrubbing. Additionally, during each scrubbing step, the fluid chamber 20 may be rotated clockwise and/or counter-clockwise so that the meniscus of the fluid in the chamber is drawn across the collection surface. Each time the meniscus passes over an area of the collection surface 21, the meniscus may agitate some of the entrapped bystander cells 154, thereby separating the bystander cells from the target cells.

After the target cells are collected and the fluid is drained from the fluid chamber, the collected cells are re-suspended in fluid. For example, buffer may be pumped into the fluid chamber and the fluid chamber may be separated from the magnetic assembly 120. Specifically, the linear actuator 90 may be operated to translate the fluid chamber 20 away from the magnetic assembly so that the magnetic assembly does not impart sufficient magnetic force to attract the target cells. Once the fluid chamber is moved away from the magnetic field, the target cells release from the collection surface so that the target cells are in suspension with the buffer. The fluid can then be drained from the fluid chamber into a collection reservoir to accumulate the target cells in the collection reservoir.

As described above, the target cells remain collected on the collection surface while the target cells are scrubbed and then drained away. Alternatively, after the cells are collected and the fluid is drained, the fluid chamber may be re-filled with buffer as described previously. The fluid chamber may then be moved out of operative engagement with the magnetic assembly 120 so that the collected cells fall into suspension with the fluid. However, rather than draining the cell suspension, the fluid chamber is moved back into operative engagement with the magnetic assembly to collect the target cells against the collection surface once again. Since a significant number of bystander cells were drained from the fluid chamber during the previous step of draining the fluid chamber, there are fewer bystander cells remaining in the cell suspension during the second step of applying a magnetic field to the cell suspension. Since there is a lower concentration of bystander cells during the second step of magnetic separation, fewer bystander cells will be entrapped on the collection surface. After the second step of applying a magnetic field, the cells may be processed as previously discussed. In particular, the fluid may be drained from the fluid chamber to drain the bystander cells while the target cells remain collected on the collection surface 21 by the magnetic field. The cells may then be scrubbed by meniscus scrubbing to separate bystander cells entrapped on the collection surface as described above. Additionally, it should be appreciated that in certain applications it may be desirable to repeat the magnetic separation step more than twice before draining the target cells. With each step of magnetic separation, the concentration of bystander cells is reduced, thereby reducing the likelihood of bystander cells being entrapped on the collection surface.

Two of the issues to consider during the magnetic cell separation procedures relate to bystander cells. One issue is cell entrapment that can occur if non-target cells are entrapped within layers of target cells during collection. The other is non-target cells literally lying on the surface of targeted cells or being loosely adhered to the target cells accumulated at the collection surface. With regard to these two issues, there are benefits to incorporating the use of gravity in separation procedures. For example, in a simple cell separation procedure with a water-like density medium containing less than 1% protein additives, RBCs settle at a rate of about 20 cell diameters per minute. In magnetic separations using ferrofluid-labeled cells, separations typically take 10 minutes. Thus an RBC falls about 200 diameters in that time period and this calculation suggests less RBC entrapment with target cells when collection occurs at an upper surface (i.e., the target cells are pulled against gravity). Contrariwise, RBC settling on a collection surface in the case where target cells are pulled downwards likely leads to more RBC entrapment. A second benefit that gravity can confer relates to emptying of the collection vessel since it can be more difficult to empty a vessel when targeted cells are on the bottom surface of a vessel as care must be taken to remove the non-magnetic contents without disturbing the collected cells. In a simple demonstration of that effect, RBC suspensions at 10% hematocrit were placed in cuvettes, tilted to a 45° angle and the contents removed with Pasteur pipettes. In one case, simulating a situation where cells might be layered on the bottom inner surface of the cuvette, care was taken to avoid touching that surface during content removal and subsequent wash medium additions. In the case simulating cells collected on the inner upper surface of the cuvette, those conditions were not required and the cuvette could be emptied more effectively and to some degree refilled more rapidly. When simulating a situation where cells collect on the inner upper surface of the cuvette, after removing the contents, refilling the cuvette two times with medium and with no mixing, the cuvette was effectively free of RBCs. In the case of simulating cell collection on the inner bottom surface, at least twice as many medium exchanges (approximately 4-5) were required to wash the cuvette free of RBCs.

FIGS. 1-4 depict an apparatus that can be used to process a leukapheresis product containing approximately $10^{10}$ cells to obtain enriched CD3+ T cells. The process uses a direct immunomagnetic labeling step, employing an anti-CD3-conjugated ferrofluid. To begin, 80 ml of platelet-free leukapheresis product ($1.2 \times 10^8$ cells/nil) is introduced to the container through a port. The container which is in an approximately vertical position is filled to approximately 30% of its capacity. While in that position, an appropriate amount of ferrofluid (e.g., 20 ml) is added to the container. Next, the chamber is rotated to a horizontal position and moved back and forth to achieve mixing.

The collection surface of the chamber may have an area commensurate with the number of cells being separated such that less than five layers, preferably less than 3 layers, are collected during the separation process. By providing sufficient area for collection, limiting the number of cells collected, and applying a magnetic field to pull cells upwards, the entrapment of bystander cells can either be eliminated or minimized to within acceptable levels. In one embodiment, with a collection surface that is 16.5×26 cm, it can be shown that $6.5 \times 10^8$ cells can be monolayered (based on our observation that $1.5 \times 10^6$ leukocytes can be monolayered in 1.0 cm²). Those calculations indicate that for a leukapheresis product of $10^{10}$ cells where 30% are CD3+ cells, approximately 4.5 layers of CD3+ target cells would accumulate at the collection surface.

In the case of an indirect immunomagnetic labeling procedure carried out through simultaneous addition of monoclonal (mAb) and a common-capture ferrofluid, anti-CD3 mAb and rat anti-mouse Fc-conjugated ferrofluid are introduced to the chamber containing the cell suspension. For this process, the chamber would be in a near vertical position as in FIG. 2 and the leukapheresis product would be introduced as indicated above, followed by the addition of approximately 5 ml of a suspension containing common-capture ferrofluid. Mixing of these components is achieved similarly to that for the direct labeling process; that is, the chamber is rotated to a horizontal position (FIG. 1) and moved back and forth. Note that no reaction or specific binding takes place during this time between the common-capture agent and target cells. For the addition of mAb, the chamber is rotated to near vertical as in FIG. 2, approximately 15 ml of a suspension containing mAb is added rapidly, the chamber is rotated to a horizontal position as in FIG. 1, and the components are mixed well by moving the container back and forth. Alternatively, the order of component addition could be modified such that common-capture ferrofluid is first added to the chamber, followed by mAb, and after appropriate mixing, the leukapheresis product is added to the chamber.

At this point, there are two options for proceeding: (1) the reactive mixtures can be left to incubate for 15-20 min, in which case some mild linear movement of the chamber is beneficial or (2) labeling of target cells with magnetic particles can be enhanced by a process that translates the magnetic particles through the cell suspension creating movement relative to cells. The latter option can be achieved by applying a magnetic gradient to the chamber as shown in FIG. 3. By bringing the chamber in proximity to the magnet for periods of 10-40 seconds followed by separation of the chamber and magnet to permit redistribution of the mixture, the reagents and cells are moved through the mixture to promote interactions. Thus, performing these steps in cycles leads to enhanced magnetic labeling of target bioentities. In small-scale experiments, effective target cell labeling can be achieved in 7-10 min.

Once incubation is complete, fresh medium is added to the chamber to dilute the contents. In this example, adding 200 ml of medium to obtain a final volume of approximately 300 ml (at $3 \times 10^7$ cells/ml) has been found to be effective for isolating 30% of the population. The container may then be rotated to a horizontal position and moved back and forth to promote mixing. Note that there is an air space in the chamber even after diluting the contents with additional buffer. Similar to the configuration shown in FIG. 3, the fluid chamber 21 is in contact with the plate magnetic array at approximately 45° to effect target-cell separation, after which non-target cells are removed by emptying the container (see FIG. 5C).

To remove entrapped bystander cells, the accumulated target cells are retained at the collection surface by maintaining the magnetic gradient. Medium is then introduced into the chamber at a rate that promotes meniscus scrubbing of the target cells accumulated on the collection surface. The chamber may be emptied again, and this step can be repeated as necessary to free entrapped cells. Finally, to recover target cells, the chamber is moved away from the magnet and medium is added to the chamber. Additionally, the chamber may be rotated or moved back and forth while horizontal to promote re-suspension of the target cells in the medium (FIG. 1).

In the event that meniscus scrubbing is not adequate for the removal of bystander cells in certain cell separation procedures, another manipulative process can be incorporated. In this instance, cells are accumulated at the collection surface as described above, the container is emptied and then reconstituted with a sufficient amount of medium, and the chamber and magnet are separated such that collected cells experience no magnetic gradient forces. As a result, the cells fall away from the collection surface and bystander cells escape entrapment. This is followed by restoring the magnetic gradient, draining the contents of the chamber, and repeating the process, as necessary, to further enrich the target cell population.

It is desirable to avoid, or at least to minimize, target cells accumulating at the collection surface in piles, such as what occurs on a collection surface that is exposed to a magnet that generates a magnetic gradient that is not homogeneous. This piling effect complicates removal of bystander cells that are entrapped during the magnetic separation process. On the other hand, when cells collect uniformly, bystander cells can be removed by passing wash medium across the collection surface while target cells are magnetically held in place (referred to as an "in-field wash"). The ability to perform in-field washes is highly desirable as it is significantly faster than traditional cell re-suspensions and subsequent magnetic separation as a means for removing entrapped bystander cells. Furthermore, it is a gentler process and, accordingly, preserves cell integrity and viability.

The following examples are provided to illustrate certain embodiments of the invention. They are not intended to limit the invention in any way.

Example 1

The Effect of Gravity on Entrapment of RBC During Magnetic Separation of Target Cells For these experiments, CD3+ cells from a CEM cell line (T-lymphoblast, CD3+) were labeled at $10^8$ cells/ml with biotinylated anti-CD3 mouse mAb (Tonbo biotech, San Diego, CA), unbound mAb was removed by washing and centrifugation, and cells were magnetically labeled with streptavidin ferrofluid by routine methods. All experiments were done at room temperature. To simulate separations from buffy coats, labeled cells were mixed with fresh bovine erythrocytes in a proprietary buffer. Those RBCs had been recovered from the pellet of centrifuged bovine blood that had been treated with EDTA. Contamination levels of RBC were simulated at 10, 20 and 30% hematocrit. Final volumes for these experiments were 2 ml and separations were done in acrylic cuvettes (1.0×1.0×4.0 cm). From the input numbers of target cells, the geometry of separation and the collection surface area used in these experiments, it was calculated that target cells (if uniformly collected) could be collected in three layers. That value is based on using the value of $1.4 \times 10^6$ cells/cm$^2$ when cells are monolayered—a number based on theoretical calculations and microscopic observation. The percentage of target cells captured in these experiments was above 94% in all cases. Thus, there is opportunity to entrap RBCs during magnetic separation.

FIG. 3 depicts the experimental design for determining entrapment of RBCs when target cells are separated with and against gravity. As noted, in cell separation processes where gravity is a component, it can be beneficial to place the magnet such that gradient forces are at a near 45° angle. Alternatively, when magnetically labeled cells are pulled downwards by a magnet, the vector forces are at 45° angle to each other and pointed in the same direction. When target cells are pulled upwards the vectors are also at a 45° angle to each other but in opposing direction. For the separation part of this experiment, cell mixtures in cuvettes were positioned at 45° angles where in one case the magnetic gradient pulls cells upwards to a collection surface (FIG. 5B), and in the other it pulls cells downward to a collection surface on the bottom of the chamber (FIG. 5A). In the former case (FIG. 5B), when target cells are pulled upwards, there is the possibility that gravity will cause non-targeted cells (RBCs in this case) to fall away as separated cells are brought upwards to the separation surface. Alternatively, for the separation depicted in FIG. 5A, RBCs that are either on the bottom of the vessel at the start of separation or that settle there by gravity during the course of separation have the opportunity to be entrapped.

For this example, once separations were complete and because it had been determined that the separation chambers (cuvettes) can effectively be washed free of RBC when there are no restrictions, such as might be the case when cells are collected on the inner surface of the lower side of the cuvette (as depicted in FIG. 5C), the entire system was turned so as to have the same orientation as that of FIG. 5C. With both separation systems in the same orientation, the contents of the cuvettes were removed with Pasteur pipettes, 3.0 mls wash buffer was added and allowed to sit 2 minutes. This WWOR process was repeated a second time and finally cuvettes were removed from the magnetic gradient and target cells were re-suspended in buffer.

To determine entrapment of RBCs, recovered cells were suspended in buffer, spun down by centrifugation and re-suspended in water to lyse entrapped RBCs. Suspensions were centrifuged to pellet targeted CEM cells and the cell free supernatants read at the Soret band for hemoglobin (400 nm). Results are given in the table below.

| magnetic separation | With g | With g | With g | Against g | Against g | Against g |
|---|---|---|---|---|---|---|
| Hematocrit | 10% | 20% | 30% | 10% | 20% | 30% |
| Red Cells entrapped: Soret band absorbance | 0.175 | 0.278 | 0.387 | 0.030 | 0.071 | 0.050 |

Since cells separated in an upward direction (against gravity) or in a downward direction (with gravity) are both freed of unbound or bystander cells in the same fashion by a surface washing technique which has been shown to be very effective, the differences in the Soret values must reflect RBCs that are entrapped during the course of separation. For separations done by pulling cells against gravity, the Soret values of 0.030, 0.071 and 0.050 for the increasing hematocrits indicate that RBC entrapment was effectively negligible. On the other hand, the very clear relationship between Soret absorbance and hematocrit is evidence that separating cells downwards (with gravity) leads to entrapment of RBC. It is difficult to determine in the case of the with-gravity separation how much of the RBC entrapment occurred because RBCs are already on the separation surface before separation begins or how many settle there during the course of the 10 minute separation procedure.

In this example, during the WWOR step, buffer was allowed to be in contact with magnetically held target cells for 2 minutes. The purpose for allowing the buffer to be in contact with target cells for that period of time was to give any target cells that might have been dislodged from the collection surface during wash addition an opportunity to be drawn back to the collection surface. Additionally, it might give any entrapped RBCs more time to settle by gravity. To determine if the time period (dwell) that the wash was in contact with the collected cells is a factor, two additional wash dwells were investigated—a 30 second dwell and a 10 minute dwell. In all instances (30 seconds, 2 minutes, and 10 minutes), recovered target cells were found to be effectively free of RBCs.

Example 2

The Effect of Gravity on RBC Contamination of CD3+ Cells Recovered from a Buffy Coat As noted above, when target cells are isolated from buffy coats, ridding the product of RBCs can require multiple cycles of re-suspension and magnetic separation. To determine whether or not the methods disclosed, specifically separating against gravity and WWOR, are beneficial to the process of recovering CD3+ target cells from a buffy coat, blood of a young normal male was obtained and processed as described in Example 1.

The buffy coat total white blood cell content was determined by lysing red blood cells in a small buffy coat sample with distilled water and counting the white blood cells in a hemacytometer. The CD3+ cells in the buffy coat were labeled with biotinylated anti-CD3 mouse mAb, unbound mAb removed by centrifugation and cells magnetically labeled with streptavidin ferrofluid by routine methods. Two magnetically labeled cell samples, in duplicate, were separated against gravity, as depicted in FIG. 5B for 10 minutes. Supernatants were removed from the chambers and four cycles of WWOR were applied. Here, two different dwell times were used following wash buffer addition. For one sample, buffer was in contact with the magnetically held target cells for a 30 second dwell period and, for the other sample, a 2 minute dwell period was applied. In both cases, four cycles of WWOR were used. For both samples, no RBCs were observed in the recovered positive fraction indicating that the 30 second dwell was adequate for this WWOR process.

The purity and yield of the positive (magnetically labeled) fractions were assessed by hemocytometer counting and by flow analysis (AmnisFlowSight, Millipore, Billerica, MA) using anti-CD3 PE (Tonbo, San Diego, CA). The percentage of the CD34+ cells recovered was 31+/−2.5% and 85+/−3% of the recovered cells were CD3+. Typical buffy coat CD3+ cell content is about 30%. The purity of the CD3+ targeting, about 85%, is reasonable considering that no FcR blocking reagents were added to the separation system, nor were other parameters of the separation optimized.

From the RBC experiments disclosed here, it is clear that there are advantages of separating cells against gravity when working with buffy coat preparations. In the case of pulling cells downwards, RBCs and non-target cells that are on the bottom surface (on the collection surface) are likely entrapped and, similarly, separating target cells laterally should also lead to some level of entrapment of those cells near or on the collection surface. The WWOR example of RBC entrapment, when target cells are pulled downwards, clearly demonstrates this. On the other hand, pulling cells against gravity, and conveniently with the magnetic gradient on some angle near 45°, at the very least gives cells that are near the collection surface the opportunity to settle. In fact, it would seem prudent to give a cell mixture an opportunity to settle for a short interval, e.g. a 2 minute period, prior to subjecting them to a magnetic gradient. The isolation of CD3+ cells from a buffy coat preparation where the product is free of RBCs after WWOR also demonstrates the advantages of this invention.

Given the role for gravity in magnetic separations described here, it should be clear that this invention is not limited to 1 g downwardly directed forces. It would be a simple matter to extend this concept to systems that employ centrifugal forces in similar ways to how gravity is exploited here. For example, a method of performing targeted magnetic separations in a moderate centrifugal field, where magnetic gradients are directed to the center of rotation, thus pulling magnetically targeted entities in that direction and where centrifugal forces are forcing non-targeted entities radially, could be used to achieve separations that are a one-step process. In other words, only targeted cells would be on the inner magnetic gradient collection surface while non-target cells would be at the bottom of an appropriately designed chamber. Recovery of highly purified populations would be possible as centrifugal forces can be modulated such that weakly magnetically targeted components, such as may be the case with cells that non-specifically bind magnetic nanoparticles, could be centrifuged away. Similarly, cells or other targets with different levels of bound magnetic mass could be separated.

Example 3

Isolation of CD3+ Cells from an Apheresis Product

Starting with an apheresis product of $10^{10}$ cells in a volume of about 1.0 L, platelets were initially removed as they are known to interfere with immunomagnetic separations. This can be accomplished by centrifugation or by well-known methods employing membrane technology (e.g., spinning-membrane filtration, Fresenius Kabi AG and Fresenius Kabi USA). The cells were then brought to a volume of approximately 80 ml with an appropriate buffer containing FcR blocking reagents that do not react with common-capture agents, DNAse, protein (e.g., human serum albumin), and other proprietary reagents known to reduce non-specific binding. This mixture was then introduced into the chamber while it was positioned vertically.

To the 80 ml cell suspension, an anti-CD3-conjugated magnetic particle (for direct labeling) or a common-capture magnetic particle (for indirect labeling) can be added from their respective vessels. Preferably, an indirect approach would be employed wherein a Fab or Fab' fragment of a common-capture antibody would be attached to the magnetic nanoparticle via a site on the distal end of the fragment's combining site. Fab or Fab' fragments that could be employed would ideally be directed to Fc determinants of the labeling mAb, and the fragments could be derived from various species or could be monoclonal (e.g., rat anti-mouse Fc mAb). The anti-Fc-functionalized nanoparticles would be engineered in such a way as to avoid interaction with the FcR blocking reagent, which would eliminate nonspecific nanoparticle—cell binding.

Using the indirect approach, a 5 ml solution containing 4 mg of rat anti-mouse ferrofluid was added to the 80 ml cell suspension in the chamber and followed by rotating the chamber to its horizontal position using the rotary actuators and by activating the linear actuators to create a back and forth mixing action. Immediately following this mixing, the chamber was rotated to its vertical position and a 15 ml solution containing 30 µg of anti-CD3 mAb (bringing the cell suspension to a final concentration of $10^8$ cells/mL) was added from a separate vessel, the chamber was rotated to a horizontal orientation, and again moved by activating the linear actuators to promote mixing of the chamber contents.

A separation chamber with dimensions of 20×22×0.75 cm was filled with an apheresis product, ferrofluid, and mAb to perform the labeling step. The chamber had a capacity of approximately 330 ml, such that the 100 ml of the labeling solution filled the chamber to approximately 30% of its capacity. An air-release valve fitted with a sterile filter was incorporated into the chamber design to maintain atmospheric pressure during filling of the chamber. After filling the chamber in the upright position, it was rotated 90° by the rotary actuators and agitated using the linear actuators. The chamber was then returned to the upright or vertical position, further rotated to 45° and moved laterally into close proximity of the magnetic array to perform magnetic mixing. The magnet had outside dimensions of approximately 25×30 cm and was mounted at a 45° angle with parallel NeFeB N-52-grade block magnets affixed to an iron backing plate of sufficient thickness to contain the magnetic flux. The magnets had dimensions of 20×0.5×2 cm, were separated by 3 mm aluminum spacers, and had alternating north and south poles, which created strong magnetic field gradients that draw magnetic material upwards toward the surface of the magnet. The process of magnetic mixing followed by agitation was repeated multiple times to magnetically mix and redistribute the cells and labeling components.

Following incubation, the cellular suspension was diluted with medium in the same chamber used for labeling, and magnetic separation was performed using the same magnet that was used for magnetic mixing. The final volume of the diluted separation solution was about 300 ml, filling the chamber to approximately 90% of its capacity. To perform magnetic separation, the chamber was rotated 45° from its upright position using the rotary actuators, then moved laterally using the linear actuators into the magnetic field. As described previously, strong magnetic field gradients draw magnetic material upwards, causing cells to collect on the chamber surface nearest to the magnet. At this point, the chamber was drained and refilled as necessary to remove non-target cells, thereby improving the purity of isolated target cells accumulated at the collection surface. Finally, the chamber was moved away from the magnet, rotated flat such that the collection surface was on the bottom, lightly agitated to re-suspend the collected cells, and drained in the upright position to recover target cells into a container.

In order to separate CD3+ cells from $10^{10}$ cells (i.e., approximately $3 \times 10^9$ target cells) using the indirect approach described above, 30 µg of anti-CD3 mAb and 4 mg of rat anti-mouse Fc ferrofluid were required. It is worth noting that similar yields could be achieved using less ferrofluid if the amount of mAb used was increased (e.g., 55 µg mAb); however, ferrofluid is substantially less costly than mAb, so operating at lower levels of mAb would generally be preferred. At 30 µg of mAb, the number of mAb per target cell would be approximately 37,500. Assuming an affinity constant of $10^8$ for this mAb and its cellular determinant and based on a simple Scatchard calculation, approximately 10% mAb would be expected to be in the bound state. From elemental analysis of our ferrofluids and theoretical considerations, we have determined that 1 µg of ferrofluid comprises $2 \times 10^8$ nanoparticles. From this information, we can calculate that 4 mg of ferrofluid contains $8 \times 10^{11}$ nanoparticles, or approximately 270 nanoparticles per target cell. Finally, we have data which suggests that a cell bearing as few as 50 ferrofluid nanoparticles can be separated with the magnetic field gradient we employ. As such, there would be sufficient mAb binding and enough ferrofluid nanoparticles present to achieve separation.

An alternative indirect approach can be employed wherein mAb and rat anti-mouse ferrofluid are mixed in the chamber, immediately followed by the addition of a cell suspension with appropriate mixing. This can be accomplished by filling the chamber with a 25 ml solution containing 1 mg of rat anti-mouse ferrofluid followed by a 25 ml solution containing 100 µg of anti-CD3 mAb. Immediately following appropriate mixing as described above, 50 mL of a cell suspension containing $2\times10^8$ cells/ml can be added to the chamber.

As noted above, magnetic cell separations can be performed at target cell concentrations near $1-2\times10^7$ cells/ml. Furthermore, accumulation of separated cells at the collection surface in no more than five layers avoids entrapment of non-target cells. Preliminary experiments indicate that four layers of cells can be washed free of contaminating non-target cells without the need for re-suspension when utilizing upwards magnetic pulling. Upon dilution with buffer to 300 ml, the total cell concentration in the separation solution is about $3.33\times10^7$ cells/ml, with a target cell concentration of $1\times10^7$ cells/ml. Previously, we determined that approximately $1.4\times10^6$ cells form a monolayer on a 1 cm$^2$ surface. Therefore, a chamber with a collection surface area of 440 cm$^2$ can be sufficient to limit the number of cell layers to five or less and avoid entrapment of non-target cells. Given this collection surface area and a desired chamber capacity of 330 ml, the thickness of the separation chamber should be about 7.5 mm, which we have determined allows for effective collection of magnetically labeled cells within a 10 min collection period. Based on these calculations, suitable dimensions of the separation chamber should be about 20×22×0.75 cm.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. The supported, mixed metal oxide catalyst, its methods of preparation and use can in alternate embodiments, be more specifically defined by any of the transitional terms "comprising", "consisting essentially of" and "consisting of".

What is claimed is:

1. A method for performing magnetic separation of cells, comprising:
    providing a fluid suspension in a fluid chamber having a first end and a second end opposite the first end, wherein the fluid suspension includes magnetically labeled target cells and bystander cells;
    positioning a collection surface between the first end and the second end of the fluid chamber at a non-zero angle relative to the horizon and applying a magnetic field to the fluid chamber containing magnetically labeled target cells such that the magnetically labeled target cells are drawn to the collection surface between the first end and the second end;
    draining the fluid suspension and bystander cells suspended therein from the fluid chamber while the magnetic field retains the magnetically labeled target cells and a residual portion of the bystander cells on the collection surface;
    after draining, introducing fluid medium into the fluid chamber such that a volume of the fluid chamber is greater than a volume of the fluid medium and such that an air pocket is provided within the fluid chamber and the fluid medium has a meniscus at an upper surface of the fluid medium within the fluid chamber;
    removing the magnetic field such that the magnetically labeled target cells and the residual portion of the bystander cells are released into suspension in the fluid medium;
    agitating the fluid medium within the fluid chamber to displace the residual portion of the bystander cells from the magnetically labeled target cells by pivoting the fluid chamber back and forth about a pivot axis such that as one of the ends of the fluid chamber is raised, the opposite end of the fluid chamber is lowered;
    collection surface of the fluid chamber at a non-zero angle relative to the horizon and re-applying a magnetic field to the fluid chamber such that the magnetically labeled target cells are again drawn to the collection surface; and
    draining the fluid medium and residual portion of bystander cells suspended therein from the fluid chamber while the magnetic field retains the magnetically labeled target cells on the collection surface.

2. The method of claim 1, wherein the collection surface extends along a plane and the method includes positioning the collection surface at a 45 degree angle relative to the horizon.

3. The method of claim 1, wherein said applying and re-applying a magnetic field comprise drawing the magnetically labeled cells to the collection surface against gravity.

4. The method of claim 1, wherein removing the magnetic field comprises displacing the fluid chamber relative to a magnetic element.

5. The method of claim 4, wherein displacing the fluid chamber operates to separate the collection surface from the magnetic field of the magnetic element.

6. The method of claim 1, wherein during said pivoting, the meniscus of the fluid medium passes over an area of the collection surface.

7. The method of claim 6, wherein pivoting the chamber comprises operating a rotary actuator to pivot the fluid chamber back and forth about the pivot axis such that the air pocket within the fluid chamber is moved back and forth between the first and second ends of the fluid chamber.

8. The method of claim 1, wherein providing the fluid suspension in the fluid chamber comprises providing a fluid, target cells and bystander cells and magnetizable particles, and labeling the target cells with the magnetizable particles.

9. The method of claim 8, wherein labeling comprises applying a magnetic field to the fluid and discontinuing the magnetic field to translate the magnetizable particles through the fluid.

10. The method of claim 1, wherein the fluid chamber has a thickness and the applying and re-applying a magnetic field comprises applying a magnetic field through the thickness of the fluid chamber.

11. The method of claim 1, further comprising a step of harvesting the target cells from the fluid chamber.

12. The method of claim 1, wherein during the applying and re-applying of a magnetic field, the magnetic field is produced by a magnetic array of block magnets mounted on a magnetically conductive plate, with the polarity of the block magnets perpendicular to the magnetically conductive plate, and wherein the polarity of the block magnets within the magnetic array alternates.

13. A method for performing magnetic separation of bioentities, comprising:
providing a fluid suspension in a fluid chamber having a first end and a second end opposite the first end, wherein the fluid suspension includes magnetically labeled bioentities and bystander bioentities;
performing a primary separation process on the fluid suspension, wherein the primary separation process comprises:
applying a magnetic field to the fluid chamber to draw the magnetically labeled bioentities to a collection surface wherein movement of magnetically labeled bioentities toward the collection surface tends to entrap bystander bioentities at the collection surface with the magnetically labeled bioentities; and
performing a secondary purification process to separate the magnetically labeled bioentities on the collection surface from entrapped bystander bioentities, wherein the secondary purification process comprises:
draining the fluid suspension from the fluid chamber while the magnetic field retains magnetically labeled bioentities and entrapped bystander bioentities on the collection surface;
after draining, introducing a wash fluid into the fluid chamber such that a volume of the fluid chamber is greater than a volume of the wash fluid and such that an air pocket is provided within an upper end of the fluid chamber;
removing the magnetic field such that the magnetically labeled bioentities and entrapped bystander bioentities fall into suspension in the wash fluid;
agitating the wash fluid to displace the entrapped bystander bioentities from the magnetically labeled bioentities within the fluid chamber by pivoting the fluid chamber back and forth about a pivot axis such that as one of the ends of the fluid chamber is raised, the opposite end of the fluid chamber is lowered, and such that the air pocket within the fluid chamber is moved back and forth between the first and second ends of the fluid chamber;
positioning the collection surface of the fluid chamber at a non-zero angle relative to the horizon and re-applying a magnetic field to the fluid chamber such that the magnetically labeled bioentities are again drawn to the collection surface; and
draining the wash fluid and bystander bioentities suspended therein from the fluid chamber while the magnetic field retains the magnetically labeled bioentities on the collection surface.

14. The method of claim 13, further comprising a step of harvesting the magnetically labeled bioentities including:
introducing a fluid medium into the fluid chamber after draining the wash fluid; and
discontinuing re-applying a magnetic field,
wherein, after discontinuing re-applying a magnetic field, the magnetically labeled bioentities are released into the fluid medium from the collection surface.

15. The method of claim 13, wherein during said pivoting, a meniscus of the wash fluid passes over an area of the collection surface as the air pocket within the fluid chamber moves back and forth between the first and second ends of the fluid chamber.

16. The method of claim 13, wherein the fluid chamber has a thickness and the applying and re-applying a magnetic field includes applying a magnetic field through the thickness of the fluid chamber.

17. A method for performing magnetic separation of bioentities, comprising the steps of:
providing a fluid suspension in a fluid chamber having a first end and a second end opposite the first end, wherein the fluid suspension includes magnetically labeled bioentities and non-magnetically labeled bioentities;
positioning a collection surface between the first end and the second end of the fluid chamber at a non-zero angle relative to the horizon and applying a magnetic field to the fluid chamber containing magnetically labeled bioentities such that the magnetically labeled bioentities are drawn to the collection surface;
draining the fluid suspension and non-magnetically labeled bioentities suspended therein from the fluid chamber while the magnetic field retains the magnetically labeled bioentities and a residual portion of the non-magnetically labeled bioentities on the collection surface;
after said draining step, introducing fluid medium into the fluid chamber such that a volume of the fluid chamber is greater than a volume of the fluid medium and such that an air pocket is provided within the fluid chamber and a meniscus is provided at an upper surface of the fluid medium within the fluid chamber; and
agitating the fluid medium to induce any non-magnetically labeled bioentities on the collection surface to move into fluid phase with the fluid medium while the magnetically labeled bioentities remain on the collection surface;
wherein agitating comprises pivoting the fluid chamber about a pivot axis such that as one of the ends of the fluid chamber is raised, the opposite end of the fluid chamber is lowered, the air pocket within the fluid chamber is moved back and forth between the first and second ends of the fluid chamber, and the meniscus of the fluid medium passes over the collection surface to agitate and free non-magnetically labeled bioentities held adjacent the collection surface.

18. The method of claim 17, wherein said step of applying a magnetic field comprises drawing the magnetically labeled bioentities to the collection surface against gravity.

19. The method of claim 17, wherein during said step of applying a magnetic field, the magnetic field is produced by a magnetic array of block magnets mounted on a magnetically conductive plate, with the polarity of the block magnets perpendicular to the magnetically conductive plate, and wherein the polarity of the block magnets within the magnetic array alternates.

20. The method of claim 13, wherein during the applying and re-applying of a magnetic field, the magnetic field is produced by a magnetic array of block magnets mounted on a magnetically conductive plate, with the polarity of the block magnets perpendicular to the magnetically conductive plate, and wherein the polarity of the block magnets within the magnetic array alternates.

* * * * *